(12) United States Patent
Malecki et al.

(10) Patent No.: US 8,465,485 B2
(45) Date of Patent: *Jun. 18, 2013

(54) ENERGY BASED DEVICES AND METHODS FOR TREATMENT OF PATENT FORAMEN OVALE

(75) Inventors: William Malecki, Oakland, CA (US); Dan Francis, Mountain View, CA (US); Kenneth Horne, San Francisco, CA (US); Mark E. Deem, Mountain View, CA (US); Hanson Gifford, Woodside, CA (US); Jose Alejandro, Sunnyvale, CA (US)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/234,908

(22) Filed: Sep. 16, 2011

(65) Prior Publication Data

US 2012/0010607 A1    Jan. 12, 2012

Related U.S. Application Data

(60) Continuation of application No. 11/622,194, filed on Jan. 11, 2007, now Pat. No. 8,052,678, which is a division of application No. 10/787,532, filed on Feb. 25, 2004, now Pat. No. 7,186,251.

(60) Provisional application No. 60/458,854, filed on Mar. 27, 2003, provisional application No. 60/478,035, filed on Jun. 11, 2003, provisional application No. 60/490,082, filed on Jul. 24, 2003.

(51) Int. Cl.
*A61B 18/14* (2006.01)

(52) U.S. Cl.
USPC .............................. 606/41; 606/50

(58) Field of Classification Search
USPC ................ 606/41, 45–52, 213–216; 607/101, 607/102, 122
See application file for complete search history.

(56) References Cited

U.S. PATENT DOCUMENTS

| | | | |
|---|---|---|---|
| 2,275,167 A | 3/1942 | Bierman | |
| 2,580,628 A | 1/1952 | Welsh | |

(Continued)

FOREIGN PATENT DOCUMENTS

| | | |
|---|---|---|
| EP | 135840 | 4/1985 |
| EP | 199694 | 10/1986 |

(Continued)

OTHER PUBLICATIONS

U.S. Appl. No. 13/341,353, filed Dec. 30, 2011, Horne, et al.

(Continued)

*Primary Examiner* — Michael Peffley
(74) *Attorney, Agent, or Firm* — Oblon, Spivak, McClelland, Maier & Neustadt, L.L.P.

(57) ABSTRACT

Methods, devices and systems for treating patent foramen ovale (PFO) involve advancing a catheter device to a position in a heart for treating a PFO, bringing tissues adjacent the PFO at least partially together, and applying energy to the tissues to substantially close the PFO acutely. Catheter devices generally include an elongate catheter body, at least one tissue apposition member at or near the distal end for bringing the tissues together, and at least one energy transmission member at or near the distal end for applying energy to the tissues. In some embodiments, the tissue apposition member(s) also act as the energy transmission member(s). Applied energy may be monopolar or bipolar radiofrequency energy or any other suitable energy, such as laser, microwave, ultrasound, resistive heating or the like.

2 Claims, 18 Drawing Sheets

U.S. PATENT DOCUMENTS

| | | |
|---|---|---|
| 2,888,928 A | 6/1959 | Seiger |
| 3,490,442 A | 1/1970 | Streu |
| 3,862,627 A | 1/1975 | Hans, Sr. |
| 3,874,388 A | 4/1975 | King et al. |
| 3,906,955 A | 9/1975 | Roberts |
| 4,307,720 A | 12/1981 | Weber, Jr. |
| 4,326,529 A | 4/1982 | Doss et al. |
| 4,473,077 A | 9/1984 | Noiles et al. |
| 4,485,817 A | 12/1984 | Swiggett |
| 4,532,924 A | 8/1985 | Auth et al. |
| 4,556,065 A | 12/1985 | Hoffmann |
| 4,562,838 A | 1/1986 | Walker |
| 4,590,934 A | 5/1986 | Malis et al. |
| 4,682,596 A | 7/1987 | Bales et al. |
| 4,788,975 A | 12/1988 | Shturman et al. |
| 4,798,594 A | 1/1989 | Hillstead |
| 4,832,048 A | 5/1989 | Cohen |
| 4,884,567 A | 12/1989 | Elliott et al. |
| 4,895,565 A | 1/1990 | Hillstead |
| 4,911,159 A | 3/1990 | Johnson et al. |
| 4,919,129 A | 4/1990 | Weber, Jr. et al. |
| 4,929,246 A | 5/1990 | Sinofsky |
| 4,976,711 A | 12/1990 | Parins et al. |
| 4,986,889 A | 1/1991 | Charamathieu et al. |
| 5,041,095 A | 8/1991 | Littrell |
| 5,042,707 A | 8/1991 | Taheri |
| 5,055,100 A | 10/1991 | Olsen |
| 5,056,517 A | 10/1991 | Fenici |
| 5,057,107 A | 10/1991 | Parins et al. |
| 5,071,417 A | 12/1991 | Sinofsky |
| 5,071,418 A | 12/1991 | Rosenbaum |
| 5,078,717 A | 1/1992 | Parins et al. |
| 5,099,827 A | 3/1992 | Melzer et al. |
| RE33,925 E | 5/1992 | Bales et al. |
| 5,125,928 A | 6/1992 | Parins et al. |
| 5,156,608 A | 10/1992 | Troidl et al. |
| 5,156,613 A | 10/1992 | Sawyer |
| 5,171,311 A | 12/1992 | Rydell |
| 5,195,959 A | 3/1993 | Smith |
| 5,196,007 A | 3/1993 | Ellman et al. |
| 5,197,963 A | 3/1993 | Parins |
| 5,207,670 A | 5/1993 | Sinofsky |
| 5,209,756 A | 5/1993 | Seedhom et al. |
| 5,290,278 A | 3/1994 | Anderson |
| 5,292,362 A | 3/1994 | Bass et al. |
| 5,295,955 A | 3/1994 | Rosen et al. |
| 5,300,065 A | 4/1994 | Anderson |
| 5,336,221 A | 8/1994 | Anderson |
| 5,336,252 A | 8/1994 | Cohen |
| 5,342,413 A | 8/1994 | Hirschberg et al. |
| 5,345,935 A | 9/1994 | Hirsch |
| 5,370,675 A | 12/1994 | Edwards et al. |
| 5,380,304 A | 1/1995 | Parker |
| 5,383,917 A | 1/1995 | Desai et al. |
| 5,405,322 A | 4/1995 | Lennox et al. |
| 5,409,479 A | 4/1995 | Dew et al. |
| 5,409,481 A | 4/1995 | Poppas et al. |
| 5,500,012 A | 3/1996 | Brucker et al. |
| 5,505,730 A | 4/1996 | Edwards |
| 5,507,744 A | 4/1996 | Tay et al. |
| 5,507,802 A | 4/1996 | Imran |
| 5,540,677 A | 7/1996 | Sinofsky |
| 5,569,239 A | 10/1996 | Sinofsky |
| 5,571,088 A | 11/1996 | Lennox et al. |
| 5,571,216 A | 11/1996 | Anderson |
| 5,575,772 A | 11/1996 | Lennox |
| 5,584,872 A | 12/1996 | LaFontaine et al. |
| 5,611,794 A | 3/1997 | Sauer et al. |
| 5,620,481 A | 4/1997 | Desai et al. |
| 5,626,607 A | 5/1997 | Malecki et al. |
| 5,662,643 A | 9/1997 | Kung et al. |
| 5,665,109 A | 9/1997 | Yoon |
| 5,669,934 A | 9/1997 | Sawyer |
| 5,680,860 A | 10/1997 | Imran |
| 5,693,078 A | 12/1997 | Desai et al. |
| 5,709,224 A * | 1/1998 | Behl et al. .................. 128/898 |
| 5,713,891 A | 2/1998 | Poppas |
| 5,725,522 A | 3/1998 | Sinofsky |
| 5,730,742 A | 3/1998 | Wojciechowicz |
| 5,749,895 A | 5/1998 | Sawyer et al. |
| 5,782,899 A | 7/1998 | Imran |
| 5,814,065 A | 9/1998 | Diaz |
| 5,824,015 A | 10/1998 | Sawyer |
| 5,827,265 A | 10/1998 | Glinsky et al. |
| 5,846,196 A | 12/1998 | Siekmeyer et al. |
| 5,855,312 A | 1/1999 | Toledano |
| 5,871,443 A | 2/1999 | Edwards et al. |
| 5,919,200 A | 7/1999 | Stambaugh et al. |
| 5,925,078 A | 7/1999 | Anderson |
| 5,928,266 A | 7/1999 | Kontos |
| 5,931,165 A | 8/1999 | Reich et al. |
| 5,944,738 A | 8/1999 | Amplatz et al. |
| 5,972,023 A | 10/1999 | Tanner et al. |
| 5,972,024 A | 10/1999 | Northrup, III et al. |
| 6,004,316 A | 12/1999 | Laufer |
| 6,012,457 A | 1/2000 | Lesh |
| 6,036,699 A | 3/2000 | Andreas et al. |
| 6,050,994 A | 4/2000 | Sherman |
| 6,056,760 A | 5/2000 | Koike et al. |
| 6,063,081 A | 5/2000 | Mulier |
| 6,063,085 A | 5/2000 | Tay |
| 6,083,223 A | 7/2000 | Baker |
| 6,086,570 A | 7/2000 | Aboul-Hosn et al. |
| 6,086,586 A | 7/2000 | Hooven |
| 6,087,552 A | 7/2000 | Gregory |
| 6,092,528 A | 7/2000 | Edwards |
| 6,132,429 A | 10/2000 | Baker |
| 6,149,660 A | 11/2000 | Laufer et al. |
| 6,156,032 A | 12/2000 | Lennox |
| 6,168,594 B1 | 1/2001 | LaFontaine |
| 6,211,335 B1 | 4/2001 | Owen et al. |
| 6,221,068 B1 | 4/2001 | Fried et al. |
| 6,236,875 B1 | 5/2001 | Bucholz |
| 6,257,241 B1 | 7/2001 | Wampler |
| 6,290,674 B1 | 9/2001 | Roue et al. |
| 6,302,898 B1 | 10/2001 | Edwards et al. |
| 6,323,037 B1 | 11/2001 | Lauto et al. |
| 6,325,798 B1 | 12/2001 | Edwards et al. |
| 6,355,030 B1 | 3/2002 | Aldrich et al. |
| 6,358,246 B1 | 3/2002 | Behl et al. |
| 6,375,668 B1 | 4/2002 | Gifford et al. |
| 6,383,198 B1 | 5/2002 | Hamilton |
| 6,391,048 B1 | 5/2002 | Ginn et al. |
| 6,391,049 B1 | 5/2002 | McNally et al. |
| 6,398,779 B1 | 6/2002 | Buysse et al. |
| 6,398,782 B1 | 6/2002 | Pecor et al. |
| 6,398,797 B2 | 6/2002 | Bombard et al. |
| 6,401,720 B1 | 6/2002 | Stevens et al. |
| 6,409,720 B1 | 6/2002 | Hissong et al. |
| 6,413,254 B1 | 7/2002 | Hissong et al. |
| 6,419,669 B1 | 7/2002 | Frazier et al. |
| 6,423,057 B1 | 7/2002 | He et al. |
| 6,436,088 B2 | 8/2002 | Frazier et al. |
| 6,451,013 B1 | 9/2002 | Bays et al. |
| 6,456,865 B2 | 9/2002 | Samson |
| 6,458,100 B2 | 10/2002 | Roue et al. |
| 6,475,213 B1 | 11/2002 | Whayne et al. |
| 6,482,224 B1 | 11/2002 | Michler et al. |
| 6,514,250 B1 | 2/2003 | Jahns et al. |
| 6,558,314 B1 | 5/2003 | Adelman et al. |
| 6,558,382 B2 | 5/2003 | Jahns et al. |
| 6,562,037 B2 | 5/2003 | Paton et al. |
| 6,583,117 B2 | 6/2003 | Owen et al. |
| 6,584,360 B2 | 6/2003 | Francischelli et al. |
| 6,589,237 B2 | 7/2003 | Woloszko |
| 6,606,523 B1 | 8/2003 | Jenkins |
| 6,641,604 B1 | 11/2003 | Adelman |
| 6,645,202 B1 | 11/2003 | Pless et al. |
| 6,645,225 B1 | 11/2003 | Atkinson |
| 6,648,897 B2 | 11/2003 | Hamilton |
| 6,652,518 B2 | 11/2003 | Wellman et al. |
| 6,669,693 B2 | 12/2003 | Friedman |
| 6,676,685 B2 | 1/2004 | Pedros et al. |
| 6,682,546 B2 | 1/2004 | Amplatz |
| 6,692,450 B1 | 2/2004 | Coleman |
| 6,702,835 B2 | 3/2004 | Ginn |
| 6,712,804 B2 | 3/2004 | Roue et al. |

| | | |
|---|---|---|
| 6,712,836 B1 | 3/2004 | Berg et al. |
| 6,716,211 B2 | 4/2004 | Mulier et al. |
| 6,726,718 B1 | 4/2004 | Carlyle et al. |
| 6,730,108 B2 | 5/2004 | Van Tassel et al. |
| 6,733,498 B2 | 5/2004 | Paton et al. |
| 6,736,810 B2 | 5/2004 | Hoey et al. |
| 6,755,790 B2 | 6/2004 | Stewart et al. |
| 6,770,072 B1 | 8/2004 | Truckai et al. |
| 6,776,784 B2 | 8/2004 | Ginn |
| 6,790,218 B2 | 9/2004 | Jayaraman |
| 6,846,319 B2 | 1/2005 | Ginn et al. |
| 6,887,238 B2 | 5/2005 | Jahns |
| 6,893,431 B2 | 5/2005 | Naimark et al. |
| 6,893,442 B2 | 5/2005 | Whayne |
| 6,918,908 B2 | 7/2005 | Bonner et al. |
| 6,926,716 B2 | 8/2005 | Baker et al. |
| 6,929,644 B2 | 8/2005 | Truckai et al. |
| 6,932,812 B2 | 8/2005 | Crowley et al. |
| 6,939,348 B2 | 9/2005 | Malecki et al. |
| 6,946,134 B1 | 9/2005 | Rosen et al. |
| 6,960,205 B2 | 11/2005 | Jahns et al. |
| 7,025,756 B2 | 4/2006 | Frazier et al. |
| 7,094,215 B2 | 8/2006 | Davison et al. |
| 7,165,552 B2 | 1/2007 | Deem et al. |
| 7,238,182 B2 | 7/2007 | Swoyer et al. |
| 7,367,975 B2 | 5/2008 | Malecki et al. |
| 7,914,527 B2 | 3/2011 | Malecki et al. |
| 7,922,716 B2 | 4/2011 | Malecki et al. |
| 2001/0020166 A1 | 9/2001 | Daly et al. |
| 2001/0037129 A1 | 11/2001 | Thill |
| 2001/0051803 A1 | 12/2001 | Desai et al. |
| 2002/0017306 A1 | 2/2002 | Cox et al. |
| 2002/0128672 A1 | 9/2002 | Dinger et al. |
| 2002/0143322 A1 | 10/2002 | Haghighi |
| 2002/0156472 A1 | 10/2002 | Lee et al. |
| 2003/0028189 A1 | 2/2003 | Woloszko et al. |
| 2003/0045893 A1 | 3/2003 | Ginn |
| 2003/0045901 A1 | 3/2003 | Opolski |
| 2003/0050665 A1 | 3/2003 | Ginn |
| 2003/0065364 A1 | 4/2003 | Wellman et al. |
| 2003/0069570 A1 | 4/2003 | Witzel |
| 2003/0078578 A1 | 4/2003 | Truckai et al. |
| 2003/0092988 A1 | 5/2003 | Makin |
| 2003/0093071 A1 | 5/2003 | Hauck et al. |
| 2003/0120268 A1 | 6/2003 | Bertolero et al. |
| 2003/0144652 A1 | 7/2003 | Baker et al. |
| 2003/0144694 A1 | 7/2003 | Chanduszko et al. |
| 2003/0158551 A1 | 8/2003 | Paton et al. |
| 2003/0199868 A1 | 10/2003 | Desai et al. |
| 2003/0208232 A1 | 11/2003 | Blaeser |
| 2003/0225421 A1 | 12/2003 | Peavey et al. |
| 2003/0233091 A1 | 12/2003 | Whayne et al. |
| 2004/0059347 A1 | 3/2004 | Hamilton |
| 2004/0092973 A1 | 5/2004 | Chanduszko et al. |
| 2004/0098042 A1 | 5/2004 | Devellian et al. |
| 2004/0098301 A1 | 5/2004 | Aoki et al. |
| 2004/0102721 A1 | 5/2004 | McKinley |
| 2004/0143292 A1 | 7/2004 | Marino et al. |
| 2004/0153057 A1 | 8/2004 | Davison |
| 2004/0153098 A1 | 8/2004 | Chin et al. |
| 2004/0176799 A1 | 9/2004 | Chanduszko et al. |
| 2004/0220596 A1 | 11/2004 | Frazier et al. |
| 2004/0243122 A1 | 12/2004 | Auth |
| 2004/0249398 A1 | 12/2004 | Ginn |
| 2005/0003288 A1 | 1/2005 | Sugiyama et al. |
| 2005/0021059 A1 | 1/2005 | Cole et al. |
| 2005/0033327 A1 | 2/2005 | Gainor et al. |
| 2005/0055050 A1 | 3/2005 | Alfaro |
| 2005/0065506 A1 | 3/2005 | Phan |
| 2005/0065509 A1 | 3/2005 | Coldwell et al. |
| 2005/0070923 A1 | 3/2005 | Mcintosh |
| 2005/0075665 A1 | 4/2005 | Brenzel et al. |
| 2005/0080406 A1 | 4/2005 | Malecki et al. |
| 2005/0119675 A1 | 6/2005 | Adams et al. |
| 2005/0125032 A1 | 6/2005 | Whisenant et al. |
| 2005/0171526 A1 | 8/2005 | Rioux et al. |
| 2005/0187568 A1 | 8/2005 | Klenk et al. |
| 2005/0192626 A1 | 9/2005 | Widomski et al. |
| 2005/0192627 A1 | 9/2005 | Whisenant et al. |
| 2005/0192654 A1 | 9/2005 | Chanduszko et al. |
| 2005/0209636 A1 | 9/2005 | Widomski et al. |
| 2005/0216054 A1 | 9/2005 | Widomski et al. |
| 2005/0251201 A1 | 11/2005 | Roue et al. |
| 2005/0256532 A1 | 11/2005 | Nayak et al. |
| 2005/0267495 A1 | 12/2005 | Ginn et al. |
| 2005/0267525 A1 | 12/2005 | Chanduszko |
| 2006/0009762 A1 | 1/2006 | Whayne |
| 2006/0036284 A1 | 2/2006 | Blaeser et al. |
| 2006/0052821 A1 | 3/2006 | Abbott et al. |
| 2006/0069408 A1 | 3/2006 | Kato |
| 2006/0079870 A1 | 4/2006 | Barry |
| 2006/0079887 A1 | 4/2006 | Buysse et al. |
| 2006/0173510 A1 | 8/2006 | Besio et al. |
| 2007/0088355 A9 | 4/2007 | Auth et al. |
| 2007/0287999 A1 | 12/2007 | Malecki et al. |

FOREIGN PATENT DOCUMENTS

| | | |
|---|---|---|
| EP | 0265532 | 5/1988 |
| EP | 0375556 | 6/1990 |
| EP | 0428812 | 5/1991 |
| EP | 0947165 | 10/1999 |
| GB | 1260919 | 1/1972 |
| GB | 1550676 | 8/1979 |
| GB | 2 359 024 | 8/2001 |
| WO | 85/00018 | 1/1985 |
| WO | 87/04081 | 7/1987 |
| WO | 90/04352 | 5/1990 |
| WO | 91/15996 | 10/1991 |
| WO | 92/04864 | 4/1992 |
| WO | 93/05705 | 4/1993 |
| WO | 93/15791 | 8/1993 |
| WO | 94/00178 | 1/1994 |
| WO | 98/07375 | 2/1998 |
| WO | 99/18862 | 4/1999 |
| WO | 99/18864 | 4/1999 |
| WO | 99/18870 | 4/1999 |
| WO | 99/18871 | 4/1999 |
| WO | 99/23959 | 5/1999 |
| WO | 99/49788 | 10/1999 |
| WO | 00/07506 | 2/2000 |
| WO | 00/09027 | 2/2000 |
| WO | 01/13810 | 3/2001 |
| WO | 01/78596 | 10/2001 |
| WO | 01/82778 | 11/2001 |
| WO | 03/022159 | 3/2003 |
| WO | 03/022160 | 3/2003 |
| WO | 03/026496 | 4/2003 |
| WO | 03/053493 | 7/2003 |
| WO | 03/071957 | 9/2003 |
| WO | 03/082076 | 10/2003 |
| WO | 03/094742 | 11/2003 |
| WO | 2004/019791 | 3/2004 |
| WO | 2004/043266 | 5/2004 |
| WO | 2004/069055 | 8/2004 |
| WO | 2004/082532 | 9/2004 |
| WO | 2004/091411 | 10/2004 |
| WO | 2005/006990 | 1/2005 |
| WO | 2005/027753 | 3/2005 |
| WO | 2005/034738 | 4/2005 |
| WO | 2005/074814 | 8/2005 |
| WO | 2005/046487 | 12/2005 |
| WO | 2005/115256 | 12/2005 |

OTHER PUBLICATIONS

Canadian Office Action issued Mar. 9, 2011 in Patent Application No. 2,519,785.

Office Action issued Jan. 12, 2011 in EP Application No. 04 758 391.9.

Besio et al., "Quantizing the Depth of Bioelectrical Sources for Non-Invasive 3D Imaging," IJBEM, vol. 7, No. 2, (2005), 4 pages total.

Anzola et al., "Potential Source of Cerebral Embolism in Migraine with Aura," Neurology (1999) 52(8): 1622.

Athiraman et al., "Selective Photothermal Tissue Interaction Using 805-nm Laser and Indocyanine Green in Tissue Welding," Journal of X-Ray Science and Technology, vol. 12, No. 2, (2004), pp. 117-126.

De Castro et al., "Morphological and Functional Characteristics of Patent Foramen Ovale and Their Embolic Implications," Stroke (Oct. 2002), pp. 2407-2413.

Cordis Corporation, Cordis Ducor® Lumeleo™ Electrode Catheters [brochure], Cordis Corporation, (Dec. 1984), 2 pages.

Del Sette, "Migraine with Aura and Right-to-Left Shunt on Transcranial Doppler: A Case Control Study," Cerebrovas Dis (1998) 8:327-330.

Fenner et al., "Shear Strength of Tissue Bonds as a Function of Bonding Temperature: A Proposed Mechanism for Laser-Assisted Tissue Welding," Lasers in Medical Science, vol. 7, (1992), pp. 39-43.

Godlewski et al., "Applications and Mechanisms of Laser Tissue Welding in 1995: Review," Proc. SPIE, vol. 2623, (Jan. 1996) pp. 334-341.

Gillette, "Catheter Ablation in Dysrhythmias," Cardio, (Mar. 1984), pp. 67-69.

Ho et al., "Morphological Features Pertinent to Interventional Closure of Patent Oval Foramen," J Interventional Cardiology, vol. 16 No. 1, (2003), pp. 33-34.

Kennedy et al., "High-burst-Strength, feedback-controlled bipolar vessel sealing," Surg Endosc (1998) 12:876-878.

Koenig et al., "Role of Intracardiac Echocardiographic Guidance in Transcatheter Closure of Atrial Septal Defects and Patent Foramen Ovale Using the Amplatzer® Device," J. Interventional Cardiology, (2003) 16 (1): 51-62.

Morady, "Transvenous Catheter Ablation of a Posterospetial Accessory Pathway in a Patient with the Wolff Parkinson-White Syndrome,"The New England Journal of Medicine, (Mar. 15, 1984), 310(11) 705-707.

Morandi et al., "Transcatheter Closure of Patent Foramen Ovale: A New Migraine Treatment?" J Interventional Cardiology, (2003), 16(1): 39-42.

Olson et al., "Developing an Animal Model for the Study of Fusion Using RF Energy," Proc. SPIE, vol. 5312, (2004), pp. 147-161.

Ott et al., "Comparative in Vitro Study of Tissue Welding Using a 808 nm Diode Laser and a Ho: YAG laser," Lasers Med Sci, vol. 16, (2001) pp. 260-266.

Pfleger, "Haemodynamic Quantification of Different Provocation Manoeuvres by Simultaneous Measurement of Right and Left Atrial Pressure: Implications for the Echocardiographic Detection of Persistent Foramen Ovale," Eur J Echocardiography (2001) pp. 260-266.

Polgar et al., "A New Technique for Closed-Chest Human His Bundle Ablation Using Suction Electrode Catheter and DC Shock," In: Perez Gomez F, ed. Cardiac Pacing Electrophysiology Tachyarrhythmias. Madrid, Spain: Grouz Publishers; 1985:1582-1586.

Polgar et al., "Comparison of Two Different Techniques for Closed-Chest His Bundle Ablation," In: Perez Gomez F, ed. Cardiac Pacing Electrophysiology Tachyarrhythmias. Madrid, Spain: Grouz Publishers; 1985:1578-1587.

Poppas et al., "Temperature-Controlled Laser Photocoagulation of Soft Tissue: in Vivo Evaluation Using a Tissue Welding Model," Lasers Surg Med., vol. 18, No. 4, (1996), pp. 335-344.

Stewart et al., Laser Assisted Vascular Welding with Real Time Temperature Control Lasers Surg Med., vol. 19, No. 1, (1996), pp. 9-16.

Stuart, "What's All the Flap About PFO Closure?," Start-Up: Windhover's Review of Emerging Medical Ventures, (Nov. 10, 2004), pp. 9-14.

Sztajzel et al., "Patent Foramen Ovale, a Possible Cause of Symptomatic Migraine: A Study of 74 Patients with Acute Ischemic Stroke," Cerebrovas Dis (2002) 13: 102-106.

Tang et al., "Quantitative Changes in Collagen Levels Following 830-nm Diode Laser Welding," Lasers Surg Med., vol. 22, No. 4. (1998), pp. 207-211.

Tang et al., "Morphologic Changes in Collagen Fibers after 830 nm Diode Laser Welding," Lasers Surg Med., vol. 21, No. 5 (1997), pp. 438-443.

Thomas, "Patent Foramen Ovale with Right-to-left Shunting: Echocariographic Alternatives," Eur J Echocariography (2001) 2:74-75.

Wilmhurst et al., "Effect on Migraine of Closure of Cardiac Right-to-Left Shunts to Prevent Recurrence of Decompression Illness of Illness or Stroke or for Haemodynamic Reasons," The Lancet, vol. 356, (Nov. 11, 2000), pp. 1648-1651.

Wilmhurst et al., "Relationship between Migraine and Cardiac an Pulmonary Right to Left Shunts," Clinical Science (2001) 100:215-220.

Supplementary European Search Report issued Oct. 15, 2010, in European Patent Application No. 04758391.9-1269.

Polgar, "Closed Chested Ablation of His Bundle: A New Technique Using Suction Electrode Catheter and DC Shock," Nachdruck Aus: Cardio Pacing, (1983), pp. 883-890.

U.S. Appl. No. 13/238,659, filed Sep. 21, 2011, Malecki, et al.

Office Action mailed on Feb. 5, 2013, in counterpart Canadian Application No. 2,519,785 (2 pages).

* cited by examiner

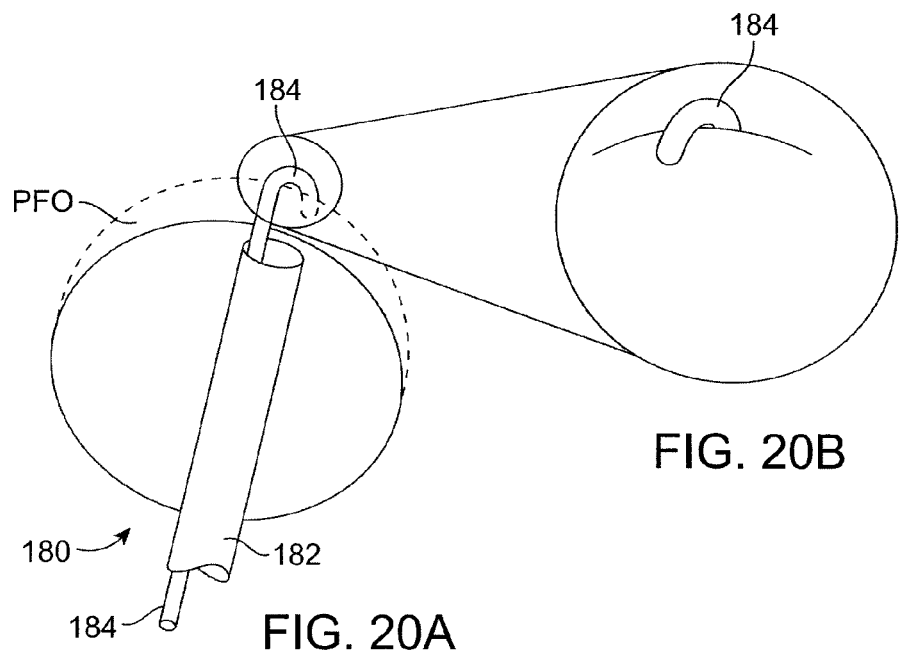
FIG. 20B
FIG. 20A
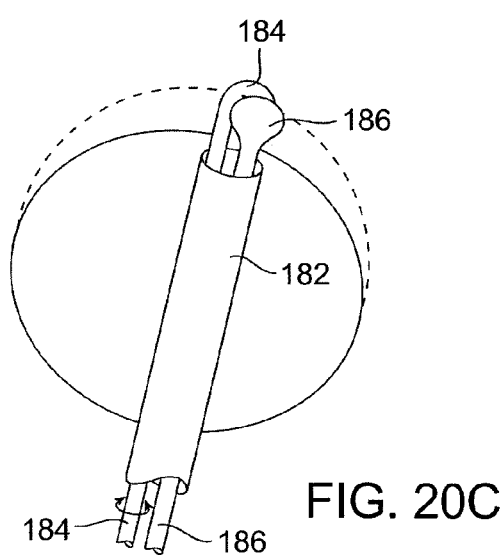
FIG. 20C

ENERGY BASED DEVICES AND METHODS FOR TREATMENT OF PATENT FORAMEN OVALE

CROSS-REFERENCES TO RELATED APPLICATIONS

This application is a continuation of U.S. patent application Ser. No. 11/622,194, now U.S. Pat. No. 8,052,678, filed Jan. 11, 2007, which is a divisional of U.S. patent application Ser. No. 10/787,532, now U.S. Pat. No. 7,186,251, filed Feb. 25, 2004, which claims priority to U.S. Provisional Patent Application Nos. 60/458,854, filed on Mar. 27, 2003; Ser. No. 60/478,035, filed on Jun. 11, 2003, and Ser. No. 60/490,082, filed on Jul. 24, 2003, the full disclosures of which are incorporated herein by reference. This application is related to U.S. patent application Ser. Nos. 10/665,974, filed on Sep. 18, 2003, and Ser. No. 10/679,245, filed on Oct. 2, 2003, the full disclosures of which are incorporated herein by reference.

BACKGROUND OF THE INVENTION

The invention generally relates to medical devices and methods. More specifically, the invention relates to energy based devices, systems and methods for treatment of patent foramen ovale.

Fetal blood circulation is much different than adult circulation. Because fetal blood is oxygenated by the placenta, rather than the fetal lungs, blood is generally shunted away from the lungs to the peripheral tissues through a number of vessels and foramens that remain patent (i.e., open) during fetal life and typically close shortly after birth. For example, fetal blood passes directly from the right atrium through the foramen ovale into the left atrium, and a portion of blood circulating through the pulmonary artery trunk passes through the ductus arteriosus to the aorta. This fetal circulation is shown in attached FIG. 1.

At birth, as a newborn begins breathing, blood pressure in the left atrium rises above the pressure in the right atrium. In most newborns, a flap of tissue closes the foramen ovale and heals together. In approximately 20,000 babies born each year in the US, the flap of tissue is missing, and the hole remains open as an atrial septal defect (ASD). In a much more significant percentage of the population (estimates range from 5% to 20% of the entire population), the flap is present but does not heal together. This condition is known as a patent foramen ovale (PFO). Whenever the pressure in the right atrium rises above that in the left atrium, blood pressure can push this patent channel open, allowing blood to flow from the right atrium to the left atrium.

Patent foramen ovale has long been considered a relatively benign condition, since it typically has little effect on the body's circulation. More recently, however, it has been found that a significant number of strokes may be caused at least in part by PFO. In some cases, stroke may occur because a PFO allows blood containing small thrombi to flow directly from the venous circulation to the arterial circulation and into the brain, rather than flowing to the lungs where the thrombi can become trapped and gradually dissolved. In other cases, thrombi might form in the patent channel of the PFO itself and become dislodged when the pressures cause blood to flow from the right atrium to the left atrium. It has been estimated that patients with PFOs who have already had cryptogenic strokes have a 4% risk per year of having another stroke.

Further research is currently being conducted into the link between PFO and stroke. At the present time, if someone with a PFO has two or more strokes, the healthcare system in the U.S. may reimburse a surgical or other interventional procedure to definitively close the PFO. It is likely, however, that a more prophylactic approach would be warranted to close PFOs to prevent the prospective occurrence of a stroke. The cost and potential side-effects and complications of such a procedure must be low, however, since the event rate due to PFOs is relatively low. In younger patients, for example, PFOs sometimes close by themselves over time without any adverse health effects.

Another highly prevalent and debilitating condition—chronic migraine headache—has also been linked with PFO. Although the exact link has not yet been explained, PFO closure has been shown to eliminate or significantly reduce migraine headaches in many patients. Again, prophylactic PFO closure to treat chronic migraine headaches might be warranted if a relatively non-invasive procedure were available.

Currently available interventional therapies for PFO are generally fairly invasive and/or have potential drawbacks. One strategy is simply to close a PFO during open heart surgery for another purpose, such as heart valve surgery. This can typically be achieved via a simple procedure such as placing a stitch or two across the PFO with vascular suture. Performing open heart surgery purely to close an asymptomatic PFO or even a very small ASD, however, would be very hard to justify.

A number of interventional devices for closing PFOs percutaneously have also been proposed and developed. Most of these devices are the same as or similar to ASD closure devices. They are typically "clamshell" or "double umbrella" shaped devices which deploy an area of biocompatible metal mesh or fabric (ePTFE or Dacron, for example) on each side of the atrial septum, held together with a central axial element, to cover the PFO. This umbrella then heals into the atrial septum, with the healing response forming a uniform layer of tissue or "pannus" over the device. Such devices have been developed, for example, by companies such as Nitinol Medical Technologies, Inc. (Boston, Mass.) and AGA Medical, Inc. (White Bear Lake, Minn.). U.S. Pat. No. 6,401,720 describes a method and apparatus for thoracoscopic intracardiac procedures which may be used for treatment of PFO.

Although available devices may work well in some cases, they also face a number of challenges. Relatively frequent causes of complications include, for example, improper deployment, device embolization into the circulation and device breakage. In some instances, a deployed device does not heal into the septal wall completely, leaving an exposed tissue which may itself be a nidus for thrombus formation. Furthermore, currently available devices are generally complex and expensive to manufacture, making their use for prophylactic treatment of PFO impractical. Additionally, currently available devices typically close a PFO by placing material on either side of the tunnel of the PFO, compressing and opening the tunnel acutely, until blood clots on the devices and causes flow to stop.

Research into methods and compositions for tissue welding has been underway for many years. Such developments are described, for example, by Kennedy et al. in "High-Burst Strength Feedback-Controlled Bipolar Vessel Sealing," Surg. Endosc. (1998) 12:876-878. Of particular interest are technologies developed by McNally et. al., (as shown in U.S. Pat. No. 6,391,049) and Fusion Medical (as shown in U.S. Pat. Nos. 5,156,613, 5,669,934, 5,824,015 and 5,931,165). These technologies all disclose energy delivery to tissue solders and patches to join tissue and form anastamoses between arteries, bowel, nerves, etc. Also of interest are a number of patents by inventor Sinofsky, relating to laser suturing of biological materials (e.g., U.S. Pat. Nos. 5,725, 522, 5,569,239, 5,540, 677 and 5,071,417). None of these disclosures, however, show methods or apparatus suitable for positioning the tissues of the PFO for welding or for delivering the energy to a PFO to be welded.

Causing thermal trauma to a patent ovale has been described in two patent applications by Stambaugh et al. (PCT Publication Nos. WO 99/18870 and WO 99/18871). The devices and methods described, however, cause trauma to PFO tissues in hopes that scar tissue will eventually form and thus close the PFO. Using such devices and methods, the PFO actually remains patent immediately after the procedure and only closes sometime later (if it closes at all). Therefore, a physician may not know whether the treatment has worked until long after the treatment procedure has been performed. Frequently, scar tissue may fail to form or may form incompletely, resulting in a still patent PFO.

Therefore, it would be advantageous to have improved methods and apparatus for treating a PFO. Ideally, such methods and apparatus would help seal the PFO during, immediately after or soon after performing a treatment procedure. Also ideally, such devices and methods would leave no foreign material (or very little material) in a patient's heart. Furthermore, such methods and apparatus would preferably be relatively simple to manufacture and use, thus rendering prophylactic treatment of PFO, such as for stroke prevention, a viable option. At least some of these objectives will be met by the present invention.

BRIEF SUMMARY OF THE INVENTION

The present invention generally provides methods, devices and systems for treating patent foramen ovale (PFO). As described in various embodiments, by using a catheter device to bring tissues adjacent the patent foramen ovale at least partially together and apply energy to the tissues, a PFO may be substantially closed acutely. By "substantially," it is meant that a stable tissue bridge will be formed across the PFO, which will withstand physiologic pressures. A substantially closed PFO, however, may still have one or more small gaps or openings, which will in at least some cases close over time via the healing process. By "acutely," it is meant that the PFO is substantially closed when the closure procedure is completed. Thus, acute closure distinguishes embodiments described below from prior techniques, which rely on delayed PFO closure via tissue healing and scarring. "Acutely," for purposes of this application, does not mean temporarily, since the various embodiments will typically provide for permanent (or at least long-term) PFO closure.

The phrase "tissues adjacent a PFO," or simply "PFO tissues," for the purposes of this application, means any tissues in, around or in the vicinity of a PFO which may be used or manipulated to help close the PFO. For example, tissues adjacent a PFO include septum primum tissue, septum secundum tissue, atrial septal tissue lateral to the septum primum or septum secundum, tissue within the tunnel of the PFO, tissue on the right atrial surface or the left atrial surface of the atrial septum and the like. By "application of energy," it is meant that energy may be transferred either to or from PFO tissues. For example, if cryogenic energy is applied, it could be said that heat energy is transferred out of the tissues. In various embodiments, any of a number of energy transfer devices and forms of energy may be used to provide such energy transfer. Types of energy used may include, for example, radiofrequency energy, cryogenic energy, laser energy, ultrasound energy, resistive heat energy, microwave energy and the like.

Application of energy to tissues to substantially close the PFO acutely may sometimes be referred to as "tissue welding." Preferably, tissue welding methods of the present invention will be performed without using tissue soldering material or other foreign material. In some embodiments, however, it may be advantageous to use one or more solder materials. Various solders and other tissue soldering matrices are described more fully in U.S. patent application Ser. No. 10/665,974, which was previously incorporated by reference. Examples of tissue solders or adhesives which may be used include, but are not limited to, autologous blood, albumin, collagen, fibrin, cyanoacrylates, mussel byssus adhesives, polymer hot melt adhesives and the like.

Embodiments described below provide for bringing tissues adjacent a PFO together (or "apposing" tissues). In various embodiments, tissues may be apposed before, during and/or after application or removal of energy to the tissues. Generally, energy application or removal will act to denature collagen in the PFO tissues. If the tissues are apposed before and/or during denaturation and/or while the collagen in the tissues is allowed to renature, the collagen in once-separated tissues binds together to bring the tissues together. Therefore, some embodiments include one or more devices for bringing (and possibly holding) tissues together before, during and/or after energy application or removal. By providing for substantial, acute closure of a PFO, devices, systems and methods may be advantageous for preventing stroke, treating migraine headaches and/or preventing or treating other medical conditions caused or exacerbated by PFO.

In one aspect of the present invention, a method of treating a PFO in a heart involves advancing a catheter device to a position in the heart for treating the PFO, bringing tissues adjacent the PFO at least partially together using the catheter device, and applying energy to the tissues with the catheter device to substantially close the PFO acutely. In some embodiments the tissues are brought together before applying the energy. Optionally, the tissues may then be held together while applying the energy. In some embodiments, the tissues may be held together after the energy has been applied as well, to allow the tissues to cool, renature, close the PFO and/or the like. Optionally, the method may further involve actively cooling the tissues after the energy has been applied.

In some embodiments, after applying energy to the tissues, the catheter device may be moved to a different position relative to the PFO, tissue may be brought together again, and energy may be applied again. Some embodiments involve multiple repetitions of the moving, bringing together and energy application steps. In such embodiments, the PFO may be substantially closed by moving along the PFO with the catheter device, typically from one side of the PFO to another, and bringing together tissues and applying energy multiple times. Such a method may be referred to as "spot welding" of PFO tissues. In some embodiments, one or more biasing members on the catheter may be used to bias the catheter toward one side of the PFO. For example, the shape of a catheter body, an expandable member, a biasing wire or the like may help urge the catheter to one side. Typically, the catheter may then be moved across the PFO, bringing tissues together and applying energy at multiple positions along the way. In one embodiment, for example, tissue apposition members (which may also be configured to apply energy to the tissues) squeeze tissue between them. As they do so, they may also squeeze a shaped catheter body between the tissues, and the cross-sectional shape of the catheter body may cause it to be urged to a new position as the tissue is squeezed down upon it. For example, the catheter body may have a triangular, oval, diamond, or other shape. After energy is applied at the first position, the tissue apposition members are moved to the second position and again squeeze down on tissue and the catheter body, thus urging the catheter body to a third position and so on.

A number of other suitable techniques are also contemplated for moving across the PFO and "spot welding" the tissues. In another embodiment, for example, a large stationary electrode is positioned either in the right or left atrium and a smaller mobile electrode is moved along the PFO in the other atrium to create spot welds. In other embodiments, one or more electrodes may be rotated around the circumference of the PFO.

Advancing the catheter device to a position in the heart for treating the PFO may be accomplished by any suitable technique. In some embodiments, for example, a first distal portion of the catheter is advanced to a location in the right atrium and that first distal portion is used for bringing tissues together. In some embodiments, a second distal portion may be advanced into or through the PFO, and the first and second distal portions are then used to appose the tissues. In some embodiments, the second portion extends through the PFO and into the left atrium, so that the first portion contacts tissue from the right atrial side and the second portion contacts tissue from the left atrial side. In various embodiments, either one or both of the portions may then be manipulated to bring the tissues together between them. For example, one or both portions may be moved axially toward one another. In some embodiments, one portion is moved axially toward the other portion, the latter portion being held relatively stationary to act as a "backstop" or surface against which to bring the tissues together. Many such backstop devices are described in patent application Ser. Nos. 60/458,854, 60/478,035, and 60/490,082, which were all incorporated by reference above. Optionally, either or both of the portions may also be used to apply energy to the tissues.

Bringing the tissues at least partially together may be accomplished by any of a number of suitable methods. For example, as just mentioned, first and/or second distal portions of the catheter device may be moved toward one another to trap, clamp, grasp, grip or otherwise appose tissues between the two members. In another embodiment, tissues may be brought together by expanding one or more expandable members. For example, one expandable member may be expanded in either the right or left atrium to push against tissue and thus bring them together. In another embodiment, one expandable member may be expanded in the right atrium and a second expanded in the left atrium, with the expansion causing the tissues to be squeezed together between the two members. A similar result may be achieved by using one expandable member and a "backstop" member, as described above. Some embodiments further include moving one expandable member toward the other to further bring the tissues together. For example, an expandable member may be slid axially toward another expandable member along the catheter device. Again, any suitable technique may be used.

In alternative embodiments, bringing the tissues together may involve deploying an expanding member within the PFO. The expanding member, such as two-pronged "fishmouthing" member, is typically disposed in a sheath while advanced into the PFO. The sheath is then retracted to allow the prongs to expand away from each other. Such expanding, "fishmouth," two-pronged members may be constructed of shape memory materials, spring-loaded materials or the like. By spreading PFO tissues laterally between two prongs, the tissues come together in the area between the prongs. In some embodiments, one or more expandable members may be coupled with the prong(s) or the catheter device to further assist in bringing the tissues together. Optionally, the method may also include contacting a left atrial surface of at least one of a septum primum and a septum secundum with a distal portion of the expanding member and retracting the expanding member to bring the tissues adjacent the PFO together. For example, the distal portion may contact the septum primum and pull it toward the right side of the heart, into contact with the septum secundum. At some point after the expanding member has been used to appose the tissues adjacent the PFO, it may be advantageous to retract the expanding member to a position within the catheter device. For example, the expanding member may be retracted in some embodiments before removing the catheter device.

In other embodiments, the first distal portion and/or the second distal portion of the catheter device may be advanced into tissues adjacent the PFO. In other words, one or more portions of the catheter device may be caused to pierce into PFO adjacent tissues. Such an embodiment, for example, may involve use of a jaw-like device, with the first and second tissue apposition members comprising opposing jaws. In one embodiment, for example, the first distal portion is advanced into septum secundum tissue. Optionally, the second distal portion may be advanced into septum primum tissue. The first and second tissue apposition members may then be moved together to bring tissues together. In yet another embodiment, a clamp-like device may be used, either with or without piercing tissues. With clamping, one portion of the clamp may contact tissue from the right atrium, and the other may contact tissue from the left atrium. Again, any of a number of other suitable techniques may be used, some of which are described more fully in U.S. patent application Ser. Nos. 60/458,854, 60/478,035, 60/490,082, 10/665,974, and 10/679,245, which were all previously incorporated by reference.

In some embodiments the catheter device may be advanced over a guidewire. The guidewire typically extends through the PFO and may include an expanding portion along its length for expanding within the PFO. Optionally, the guidewire may extend into the left atrium, and the method may optionally include contacting a left atrial surface of at least one of a septum primum and a septum secundum with a distal portion of the guidewire and retracting the guidewire to bring the tissues adjacent the PFO together.

Any suitable type of energy may be applied to the PFO tissues to provide acute PFO closure. In some embodiments, for example, monopolar or bipolar radiofrequency energy is applied, while in alternative embodiments cryogenic, resistive heat, ultrasound, microwave, or laser energy, heat energy in the form of heated fluid such as saline, or the like may be applied. Energy may be applied by energizing a single conductive member of the catheter device or multiple conductive members, in various embodiments. Generally, any suitable devices for energy delivery are contemplated. In one embodiment, applying energy to the tissues involves applying energy to a conductive fluid and releasing the conductive fluid from the catheter device to contact the tissues. For example, a conductive fluid such as saline may be introduced into one or more expandable members of the catheter device, energy such as radio frequency energy may be applied to the fluid, and the fluid may then be released from the expandable member(s) through at least one, and preferably many, small apertures on the expandable member. The energized conductive fluid then contacts the tissues to close the PFO.

Some embodiments of the method may further involve monitoring an amount of energy applied to the tissues. For example, monitoring the energy may involve monitoring a temperature of the tissues, an impedance of the tissues and/or the like. Such a method may further involve determining when a sufficient amount of energy has been applied to the tissues to acutely close the PFO. Optionally, the method may also include discontinuing the application of energy when the sufficient amount of energy has been applied.

Any of the above methods may also involve directly visualizing the PFO and the adjacent tissues using at least one visualization device coupled with the catheter device. Such a visualization device may include a fiber optic device, an ultrasound device or any other suitable visualization device.

In another aspect of the present invention, a method of treating a patent foramen ovale in a heart includes: advancing a catheter device to a position in the heart for treating the patent foramen ovale; bringing tissues adjacent the patent foramen ovale at least partially together using the catheter device; applying energy to the tissues with the catheter device while holding the tissues at least partially together; and holding the tissues at least partially together for a sufficient time after applying the energy to substantially close the patent foramen ovale. Such a method may include any of the features of the embodiments described above.

In yet another aspect of the invention, a catheter device for treating a patent foramen ovale in a heart includes an elongate catheter body having a proximal end and a distal end, at least one tissue apposition member at or near the catheter body distal end for bringing tissues adjacent the patent foramen ovale at least partially together, and at least one energy transmission member at or near the distal end for applying energy to the tissues to substantially close the patent foramen ovale acutely. In some embodiments, the at least one tissue apposition member comprises a first tissue apposition member for contacting tissue from the right atrium of the heart. Optionally, a second tissue apposition member may be included for contacting tissue either from the right atrium or the left atrium, in various embodiments. For example, in one embodiment the first and second members may comprise a set of opposable jaws that may be used from within the right atrium to bring the tissues together, optionally advancing through one or of the PFO-adjacent tissues. In other embodiments, the second member may be advanced through the PFO to contact the tissue from the left atrium. Any number of different tissue apposition members may be included.

As described above, for example, one or both of first and second tissue apposition members may comprise expandable members, and either (or both) may be axially slidable toward the other to bring tissue together between them. In other embodiments, one expandable member and one shaped deployable "backstop" member may be used. The deployable member, for example, may comprise a shape-memory device which is advanced into the left atrium and deployed to contact tissue. An expandable balloon may be expanded and possibly moved axially along the catheter to bring the tissue together between it and the deployable backstop. Any one or more of such expandable members may also include at least one small aperture for allowing conductive fluid to escape from expandable member to contact the tissues. Some embodiments include multiple small apertures, and some include two expandable members with apertures.

In other embodiments, first and second tissue apposition members are configured as arms of a clamp, with one arm disposed in the right atrium and the other in the left atrium, for clamping tissues together. Still other embodiments may include one set of opposable jaws and one hook or clamp member to bring the tissue toward the clamp. In other embodiments, the first and second members are configured as a clip, "bobby pin," or the like, wherein the relative shapes of the first and second apposition members urge the tissues together. For example, in one embodiment one of the members may be shaped as a hook or similarly curved member for hooking over the PFO to contact the tissues from the left atrium, while the other member may be relatively straight to contact the tissues from the right atrium. Tissues may thus be grasped together between the two members, bringing them together, not unlike an object placed between the tongs of a bobby pin or within the curves of a paper clip.

Some embodiments of the apparatus further include a guide member for advancing through the PFO, with the catheter device being slidably disposed over the guide member. The guide member may include, for example a guide catheter and at least one expandable member disposed within the guide catheter, wherein the guide catheter is retractable to expose the expandable member to allow it to expand within the PFO. The expandable member, in turn, may have any suitable configuration, but in some embodiments it includes at least two members that expand apart to provide lateral force to the tissues adjacent the PFO, such as a "fishmouth" or two-prong expandable member. When exposed, the expanding member may also provide dilatory force to the tissues adjacent the PFO. To provide expandability, the expandable member may be made of shape memory material, may be spring loaded, and/or the like.

In alternative embodiments, the guide member may comprise a guidewire having an expandable portion along its length. For example, the expandable portion may be a divided portion, the divided portion comprising expandable shape memory material. Optionally, the guide member may include at least one tip for contacting a left atrial surface of the tissues adjacent the PFO. Such a tip may be conformable to the left atrial surface. The guide member may be retractable to engage the at least one tip with the left atrial surface. In any of the above embodiments, one or more guide members, or component parts of a guide member, may act as one or more energy transmission members. In some embodiments, for example, an expanding member may act as a monopolar or bipolar radiofrequency electrode.

The at least one energy transmission member of the catheter device may comprise any suitable energy transmission device or combination of devices. For example, the transmission member may transmit radiofrequency energy, cryogenic energy, resistive heat energy, ultrasound energy, microwave energy, laser energy or any other form of energy for treating PFO tissues. In preferred embodiments, the energy transmission member comprises a monopolar or two bipolar radiofrequency transmission members. Such a transmission member, for example, may be curved to approximate the curvature of the PFO. In other embodiments, straight transmission members, mesh or braided transmission members, multiple pin-point transmission members or the like may be used.

In some embodiments, one or more energy transmission members are coupled with one or more tissue apposition members. In some embodiments, for example, one or more energy transmission members simply act as tissue apposition members. In some embodiments, energy transmission member is movable along at least part of a circumference of the at least one tissue apposition member. In alternative embodiments, the energy transmission member comprises a guide member for advancing through the PFO, with the catheter device being slidably disposed over the guide member. Again, the guide member typically includes at least one expandable portion for expanding within the PFO to at least partially bring together the tissues adjacent the PFO, and in some embodiments the expandable member acts as the energy transmission member(s). In still other embodiments, energy transmission members may be coupled with both the tissue apposition member and the guide member/expandable member.

As described above, in one embodiment the at least one energy transmission member include one or more energy transmission member disposed within an expandable member for applying energy to a conductive fluid. The energy transmission member further includes one or more conductive fluids which are introduced into the expandable member(s) and then allowed to escape from the expandable members, typically via multiple apertures. In various embodiments, one, two or more expandable members with apertures, conductive fluid and an energy transmission member may be included. In one embodiment, radio frequency energy is transmitted to saline solution as the conductive fluid, but in alternative embodiments other forms of energy and/or conductive fluid(s) may be used.

Some embodiments of the catheter device may further include at least one sensor coupled with the catheter device for sensing an amount of energy delivered to the tissues by the at least one energy transmission member. Sensors, for example, may be infrared sensors, thermistors, thermocouples or the like, though any sensors may be used. Optionally, a microprocessor may be coupled with the at least one sensor for processing sensed data to determine when the amount of delivered energy has reached a desired amount of energy.

In another aspect of the invention, a system for treating a patent foramen ovale in a heart includes a catheter device and at least one guide member for guiding the catheter device to a position for treating the patent foramen ovale. The catheter device includes an elongate catheter body having a proximal end and a distal end, at least one tissue apposition member at or near the catheter body distal end for bringing tissues adjacent the patent foramen ovale at least partially together, and at least one energy transmission member at or near the distal end for applying energy to the tissues to substantially close the patent foramen ovale. The catheter device may include any of the features or variations described above.

These and other embodiments are described in further detail in the following description related to the appended drawing figures.

BRIEF DESCRIPTION OF THE DRAWING FIGURES

FIGS. 20A-20C are perspective views of a distal portion of a catheter apparatus having two separate tissue apposition members according to another embodiment of the present invention;

Figure 21A:
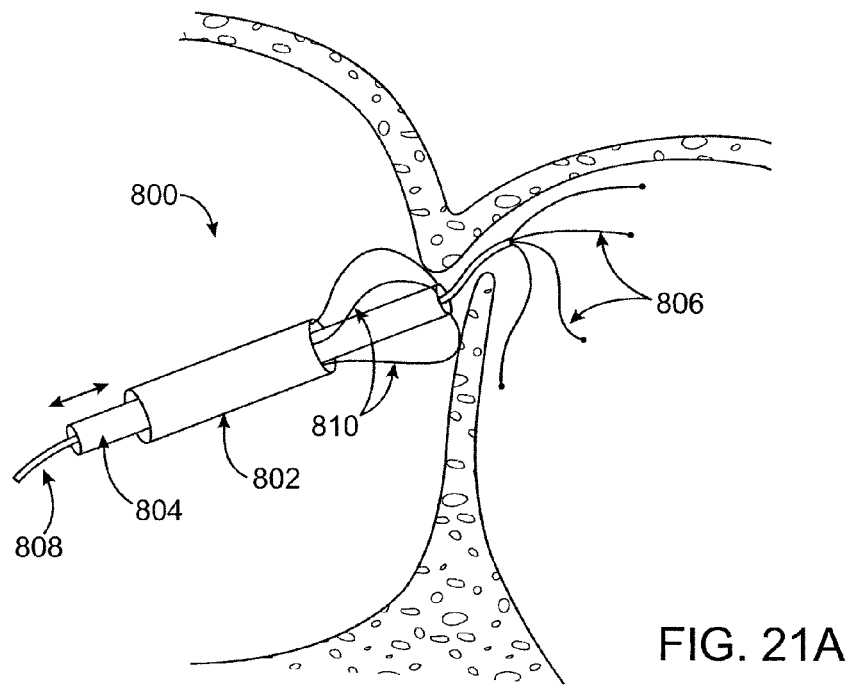
Figure 21B:
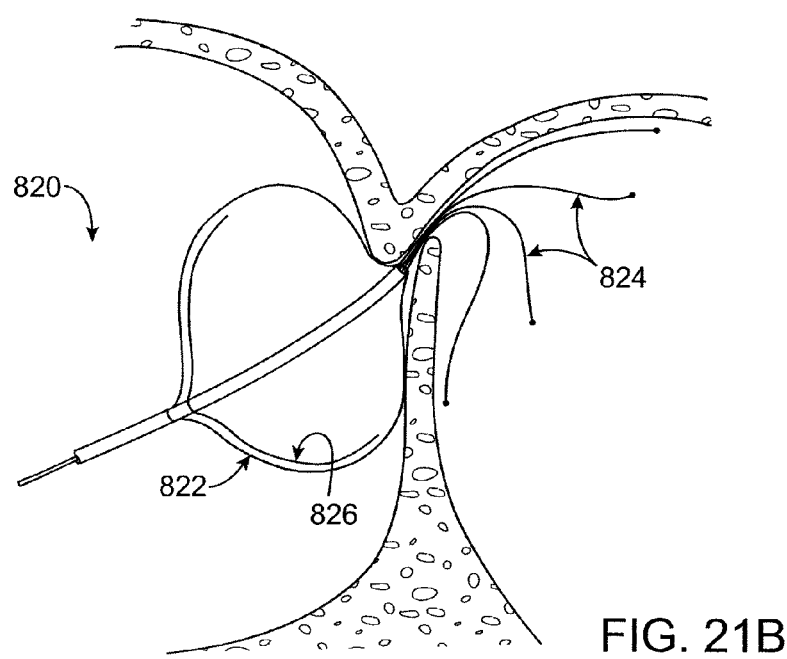
Figure 22A:
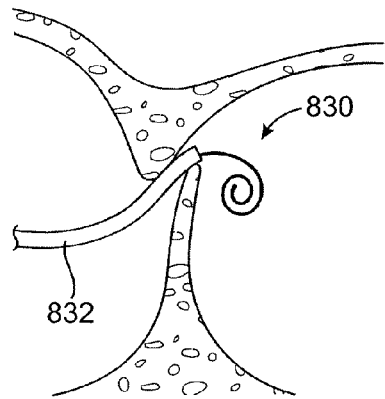
Figure 22B:
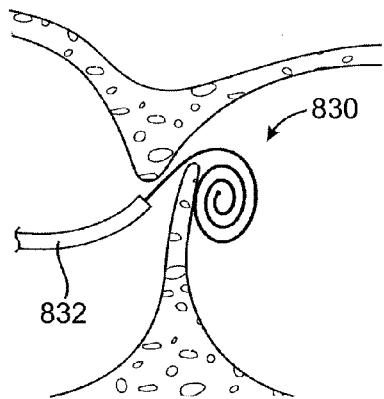
Figure 22C:
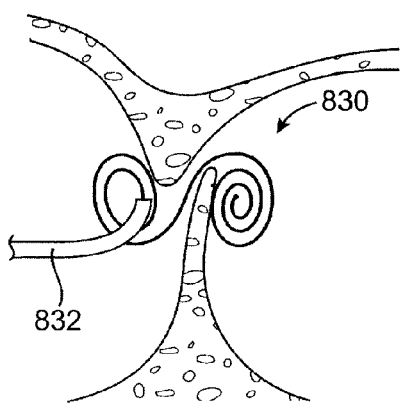
Figure 22D:
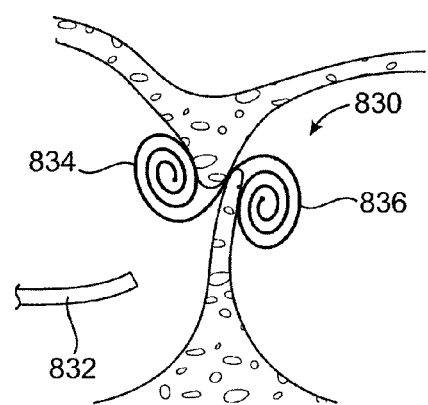
Figure 23:
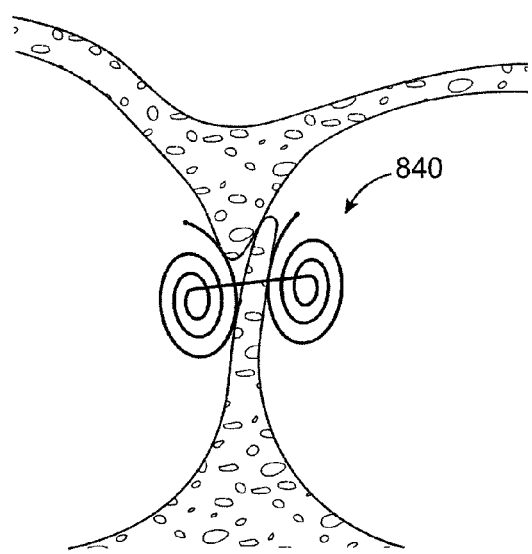
Figure 24:
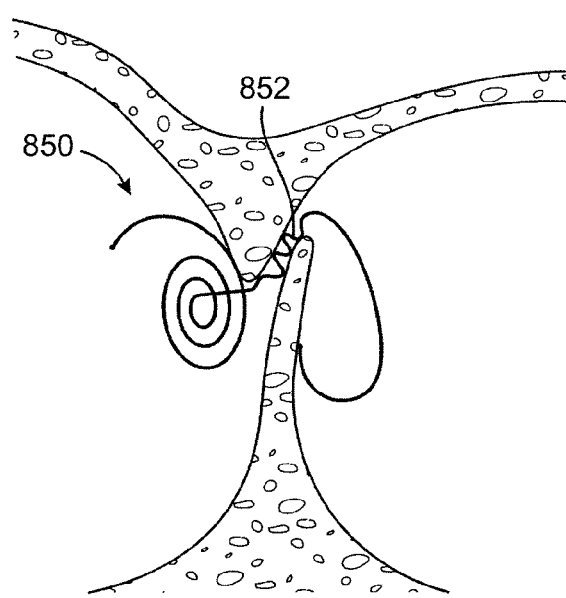

FIGS. 21A-21B demonstrate treating a PFO using a closure device having a backstop according to an embodiment of the present invention;

FIGS. 22A-22D demonstrate treating a PFO using a spring coil closure device according to an embodiment of the present invention;

FIG. 23 demonstrates treating a PFO using a spring coil closure device according to another embodiment of the present invention; and FIG. 24 demonstrates treating a PFO using a spring coil closure device according to another embodiment of the present invention.

DETAILED DESCRIPTION OF THE INVENTION

Devices and methods of the present invention generally provide for patent foramen ovale (PFO) treatment through application of energy. Methods involve advancing a catheter device to a position in the heart for treating the PFO, bringing tissues at least partially together using the catheter, and applying energy to tissues adjacent a PFO to substantially close the PFO acutely. Devices of the invention generally include a catheter device having a proximal end and a distal end, at least one tissue apposition member, and at least one energy transmission member adjacent the distal end.

Figure 1:
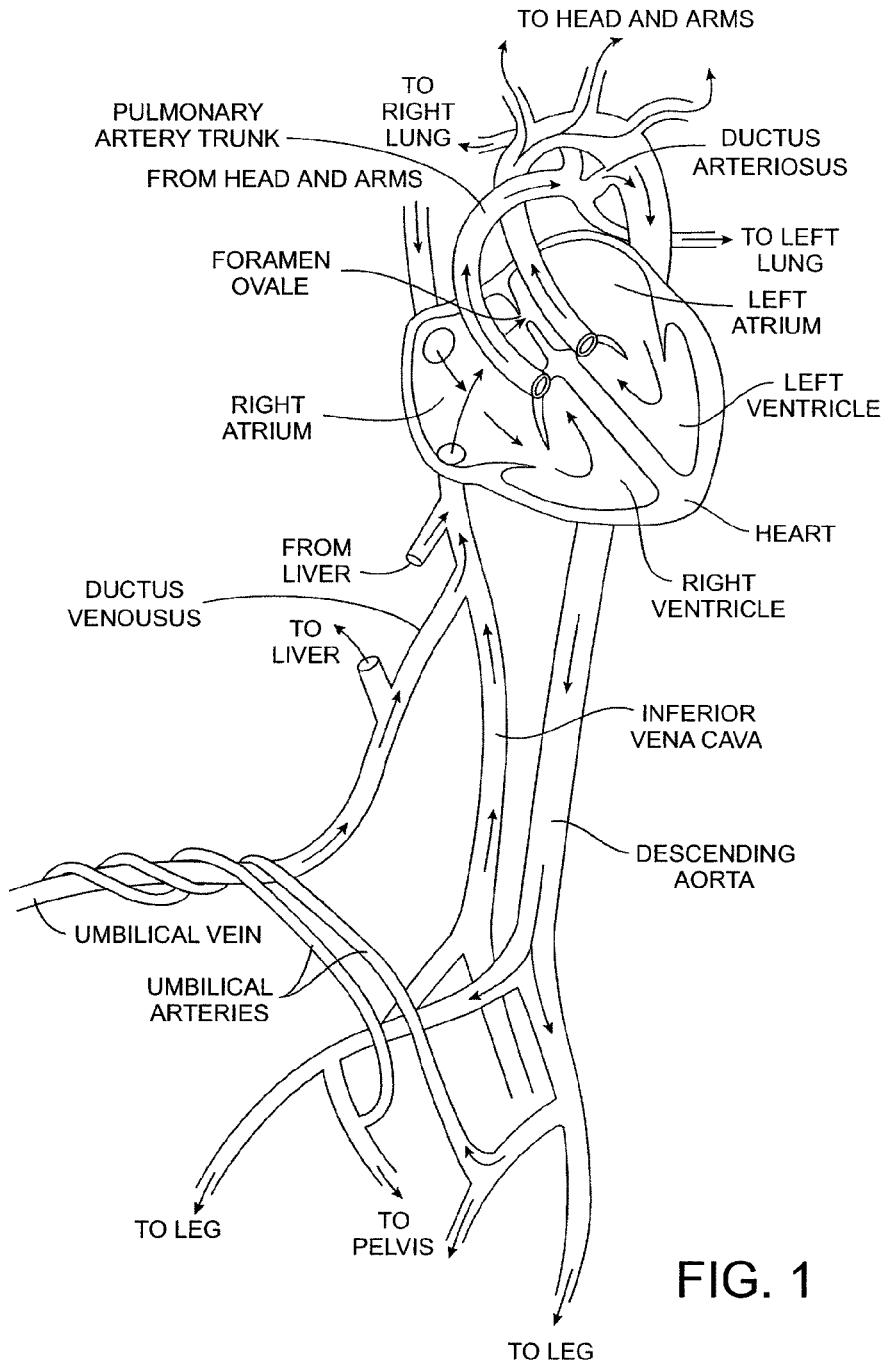
FIG. 1 is a diagram of the fetal circulation.

FIG. 1 is a diagram of the fetal circulation. The foramen ovale is shown, with an arrow demonstrating that blood passes from the right atrium to the left atrium in the fetus. After birth, if the foramen ovale fails to close (thus becoming a PFO), blood may travel from the right atrium to the left atrium or vice versa, causing increased risk of stroke, migraine and possibly other adverse health conditions, as discussed above.

Figure 2:
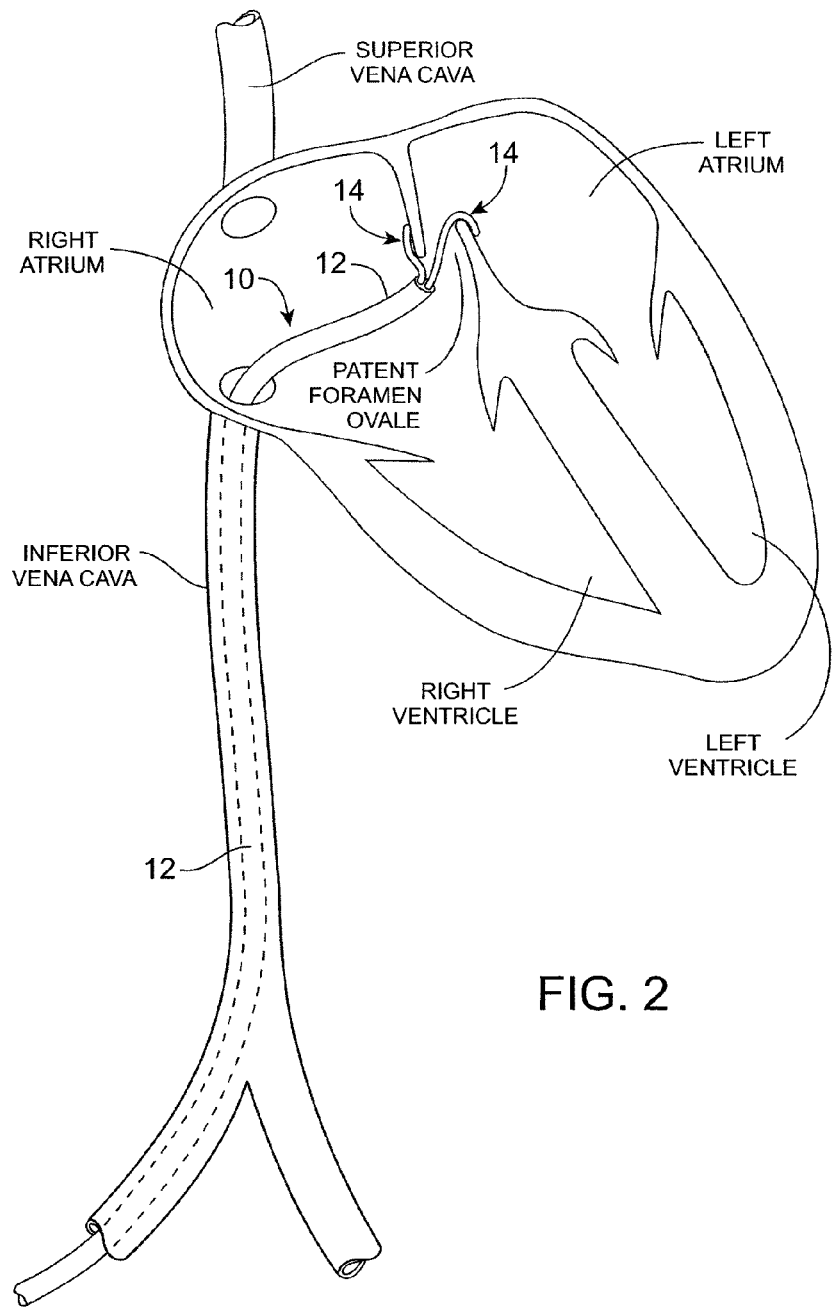
FIG. 2 is a diagram of a catheter apparatus according to an embodiment of the present invention, the catheter passing through the inferior vena cava and right atrium and through the PFO.

With reference to FIG. 2, one embodiment of a catheter device 10 for treating PFO suitably includes a catheter body 12 and one or more tissue apposition members 14. Catheter device 10 may be advanced through the vasculature of a patient to a position in the heart for treating a PFO. For example, as shown catheter device 10 has been advanced through the inferior vena cava into the right atrium of the heart. In alternative embodiments, a catheter device may be advanced through the aorta to the left ventricle and then into the left atrium of the heart to treat the PFO. In some embodiments, two separate portions of a catheter apparatus may be advanced to the right atrium and left atrium, and in yet another embodiment, a guidewire or other component of a catheter apparatus may extend from outside the patient, through the vasculature to the right atrium, through the PFO to the left atrium, and out the aorta to the vasculature to exit the patient from a second site. Various embodiments may thus make use of any suitable access technique for disposing a catheter device in a location for treating a PFO.

Catheter body 12 typically comprises an elongate, flexible body having at least one lumen. Catheter body 12 may be manufactured from any suitable material or combination of materials known in the catheter arts or hereafter discovered, such as PTFE, other polymers or the like. Catheter body 12 may also having any suitable size, profile, diameter, shape and the like. Optionally, catheter body 12 may be slidably disposed over a guide member (not shown), such as a guide catheter, guidewire, or the like. In some embodiments, such a guide member may include one or more expanding members or other similar devices for deploying within the PFO to help appose the adjacent tissues. For further description of such expandable guide members, reference may be made to U.S. patent application Ser. No. 10/679,245, which was previously incorporated by reference.

Tissue apposition members 14 generally may include any one, two or more devices for helping bring tissues adjacent the PFO together. As shown in FIG. 2, one member 14 may be disposed in the right atrium to contact tissue from the right atrial side, such as septum secundum tissue, while the other member 14 may be advanced through the PFO to contact tissue from the left atrium. In some embodiments, tissue apposition members 14 may be pre-shaped and manufactured from shape-memory material, spring stainless steel or the like, such that when they are released from catheter body 12, they take on a shape that allows them to bring the tissues together.

Catheter device 10 also includes at least one energy transmission member. In the embodiment shown, either one or both of tissue apposition members 14 may also act as energy transmission members. In various embodiments, energy transmission members may be capable of bringing the tissues together, energy transmission members may be coupled with tissue apposition members, or energy transmission members may be separate from and not coupled with tissue apposition members. Also in various embodiments, one energy transmission member may be used, such as to provide monopolar radiofrequency energy (RF), two transmission members may be used, such as to provide bipolar RF energy, or more than two transmission members may be used.

Figure 3:
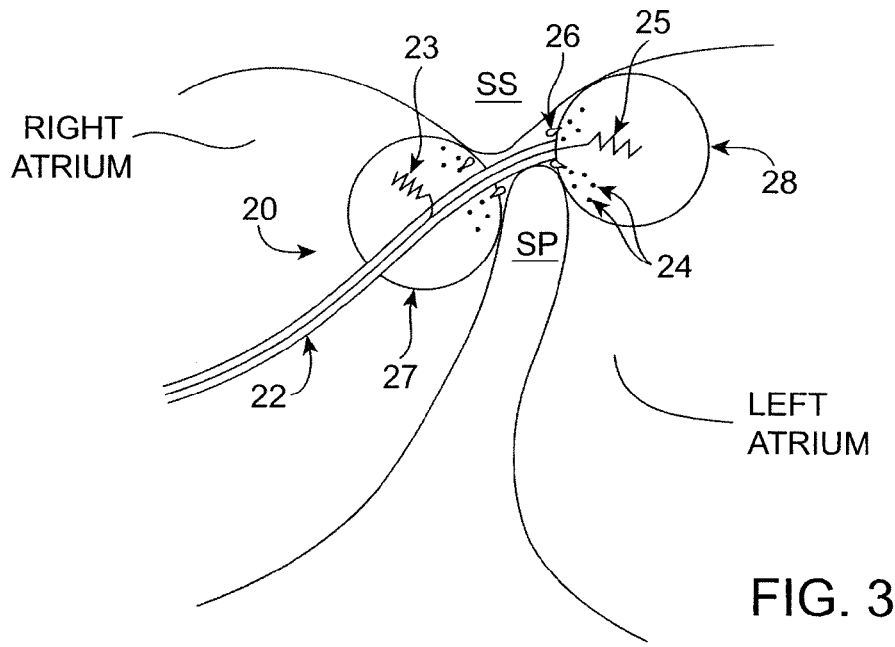
FIG. 3 is a perspective view of a distal portion of a catheter apparatus having two expandable members according to an embodiment of the present invention.

Referring now to FIG. 3, another embodiment of a catheter device 20 for PFO treatment suitably includes a catheter body 22, a first expandable member 27 having a first energy transmission member 23, and a second expandable member 28 having a second energy transmission member 25, with each expandable member 27, 28 including multiple apertures 24 for allowing passage of conductive fluid 26. Expandable members 27, 28 may be positioned for treatment, such as in the right atrium (first member 27) and the left atrium (second member 28) and then expanded to bring together tissues of the septum secundum SS, septum primum SP and/or other PFO-adjacent tissue. In some embodiments, one or both of expandable members 27, 28 may also be moved axially along catheter body 22, such as by sliding, so as to bring the tissues together between the two expandable members 27, 28. For example, second expandable member 28 may be disposed on a separate catheter body disposed over or within catheter body 22 to allow second member 28 to axially slide back and forth along catheter body 22.

Expandable members 27, 28 may comprise any suitable material or combination of materials now known or developed in the future. Expandable balloon members for use on catheters are well known, and any suitable variation may be used in various embodiments of the invention. Expandable members 27, 28 may be made of conformable elastomeric materials, polymers or the like and may have any suitable shape upon expansion.

Energy may be applied to the tissues by introducing one or more conductive fluids 26, such as saline solution or the like, into expandable member 27, 28, applying energy (such as RF energy) to conductive fluids 26 via energy transmission members 25, 27, and then allowing fluid(s) 26 to pass from apertures 24 to contact the tissues. Thus, the fluid 26 may provide the needed energy to the tissues to cause closure of the PFO. After transmitting the energy to the nearby PFO tissues, conductive fluid 26 harmlessly dissipates in the body.

In various embodiments, energy transmission members may comprise any of a number of devices and may transmit any suitable type of energy for closing a PFO. Some types of energy which may be used, for example, include radiofrequency, cryogenic, resistive heat, ultrasound, microwave and laser energy. Radiofrequency energy transmission members may be either monopolar or bipolar, with monopolar catheter devices also including a grounding member. Energy transmission members may also have any suitable configuration, many of which are described below in reference to specific embodiments. In some embodiments, energy transmission members are fixedly coupled with tissue apposition member, while in other embodiments energy transmission members are movable within tissue apposition member, for example to move about the circumference of the PFO to weld PFO tissues at multiple locations. In some embodiments, energy delivery is achieved by circulating cooled or heated fluids within expandable members 27, 28, without allowing such fluids to pass out of expandable members 27 & 28. In these embodiments, apertures 24 are eliminated from the design.

Energy transmission members 23, 25 provide sufficient energy transfer, for a sufficient time, to weld the tissues. The time span of energy transmission may be, for example, from about 0.5 seconds to about 15 minutes, and more preferably from about 30 seconds to about 5 minutes. Energy transmission, in some embodiments, may be from about 0.5 Watts to about 100 Watts, and more preferably from about 5 Watts to about 50 Watts. In various embodiments, any other suitable energy and timing combination may alternatively be used. In one experimental example, a PFO in a section of pig heart tissue used ex-vivo in a flowing saline test fixture was closed by applying suction to appose the PFO tissues and applying RF energy at approximately 25 Watts for 7 minutes. RF energy application was then discontinued, but tissue apposition was continued for an additional 1 minute to hold tissues together while cooling, thus allowing collagen in the tissues to reorganize and bind together to form a stable tissue bridge. In alternative embodiments, other energy amounts, energy application times, tissue apposition times and the like may be used.

Although any suitable type of energy may be transmitted by energy transmission members in various embodiments, some embodiments make use of monopolar or bipolar radiofrequency (RF) energy. Devices may use monopolar radiofrequency energy, for example, wherein energy is applied simultaneously to all conductive elements, completing the circuit through an external ground pad affixed to the skin of the patient. Alternatively, bipolar energy may be applied to all conductive elements simultaneously, and the circuit completed through a ground element incorporated elsewhere on the catheter device. Further embodiments may include applying bipolar energy between two or more energy transmission members, which are electrically isolated from one another within catheter device.

Control systems coupled with energy transmission members or tissue apposition members, or otherwise disposed within a catheter device, may sense an amount of energy delivered to PFO tissues and, optionally, may automatically stop energy delivery upon detecting a change in condition of energy delivery, for instance an increase in electrical resistance or impedance in PFO tissues or in the catheter device, an increased energy draw from the catheter device, and/or the like. In some embodiments, energy delivery may be automatically stopped when an amount of delivered energy reaches a desired level, such as an amount of energy sufficient to substantially close the PFO. The amount of delivered energy may be monitored by any suitable method, such as monitoring temperature or impedance in PFO tissues or the like. In some embodiments, one or more sensors coupled with tissue apposition members, energy transmission members, or any other part of a catheter device may be used for monitoring such indicia. Examples of sensor devices include but are not limited to infrared sensing devices, thermistors and thermocouples. Optionally, a control system may also include a microprocessor coupled with the sensors to determine when a desired amount of energy has been delivered and/or to automatically stop energy transmission. In alternative embodiments, a microprocessor may be attached to a catheter device which can sense, monitor and control energy delivery, thus not requiring separate sensors.

Figure 4:
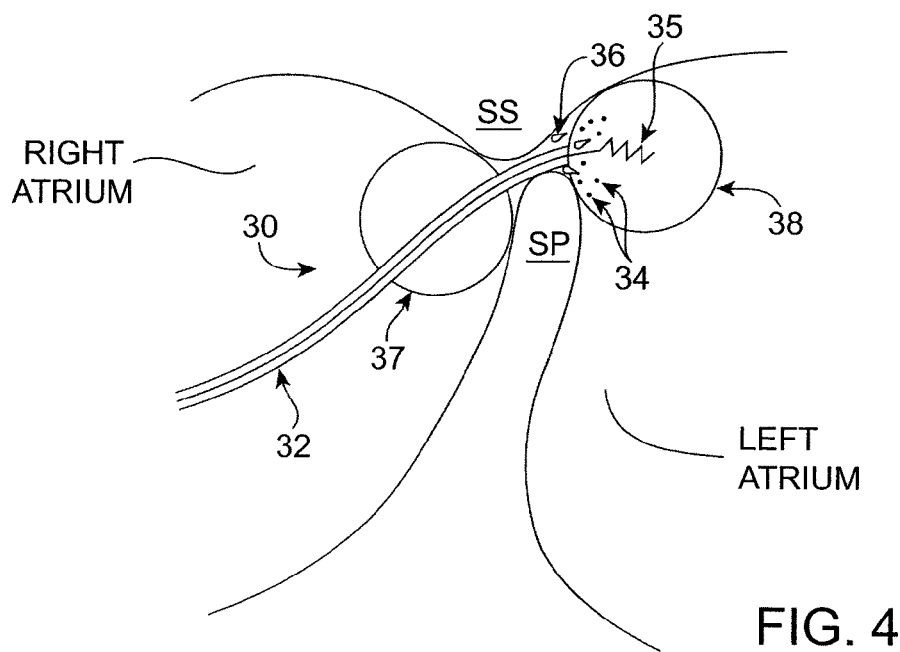
FIG. 4 is a perspective view of a distal portion of a catheter apparatus having two expandable members according to another embodiment of the present invention.

FIG. 4 shows a slightly different embodiment of a catheter device 30 having a catheter body 32, a first expandable member 37 and a second expandable member 38 having an energy transmission member 35 and multiple apertures 34 for allowing passage of a conductive fluid 36. In this embodiment, first expandable member 37 may be used as a tissue apposition member without providing additional energy transmission.

Figure 5:
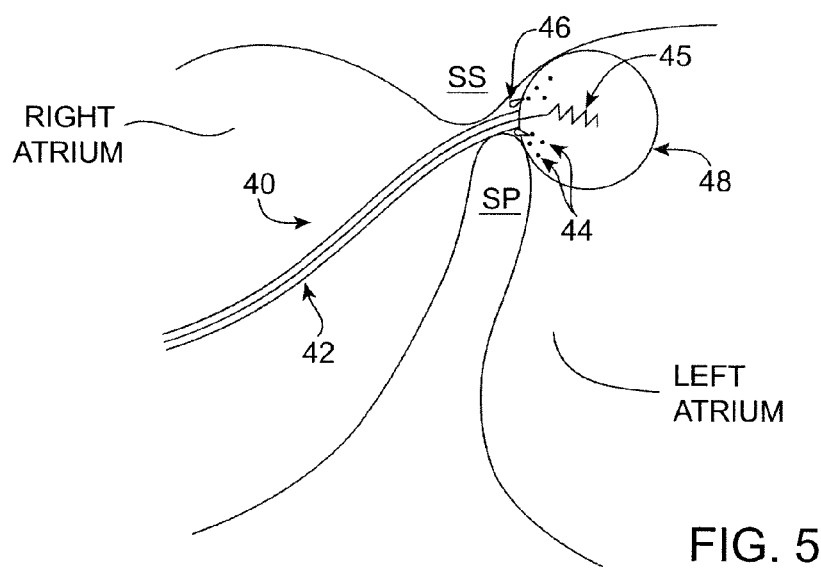
FIG. 5 is a perspective view of a distal portion of a catheter apparatus having one expandable member according to another embodiment of the present invention.

Referring to FIG. 5, an alternative embodiment of a catheter device 40 for treating PFO includes a catheter body 42, an expandable member 48 having apertures for allowing passage of fluid 46, and an energy transmission member 45. In this embodiment, expanding expandable member 48 may be sufficient to bring tissues together, or proximally directed force may be applied to expandable member 48, such as by pulling back on catheter body 42, to bring the tissues together.

Figure 6:
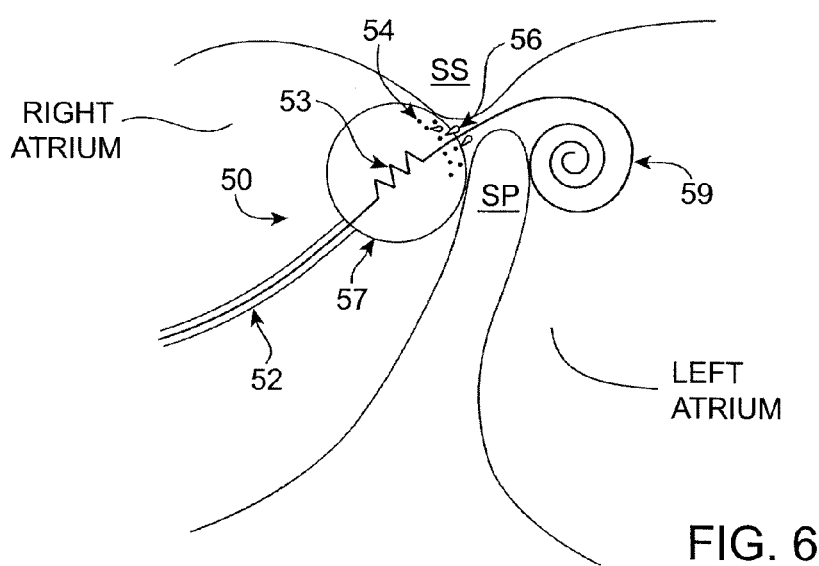
FIG. 6 is a perspective view of a distal portion of a catheter apparatus having one expandable member and a shape-memory member according to another embodiment of the present invention.

Referring now to FIG. 6, one embodiment of a catheter device 50 includes a catheter body 52, an expandable member 57 having an energy transmission member 53 disposed within it and apertures 54 on its surface for allowing passage of conductive fluid 56, and a shaped distal portion 59. Shaped distal portion 59 resides in the left atrium and acts as a surface or "backstop," such that tissue may be brought together between shaped distal portion 59 and expandable member 57. In the embodiment shown, shaped portion 59 is a helical coil, which may be made of shape memory material, spring stainless steel or the like, so that it has a relatively straight configuration while disposed within catheter body 52, but assumes the coiled configuration when released. In other embodiments, other backstop devices may be used, such as those described more fully in U.S. patent application Ser. No. 60/478,035, which was previously incorporated by reference.

Figure 7:
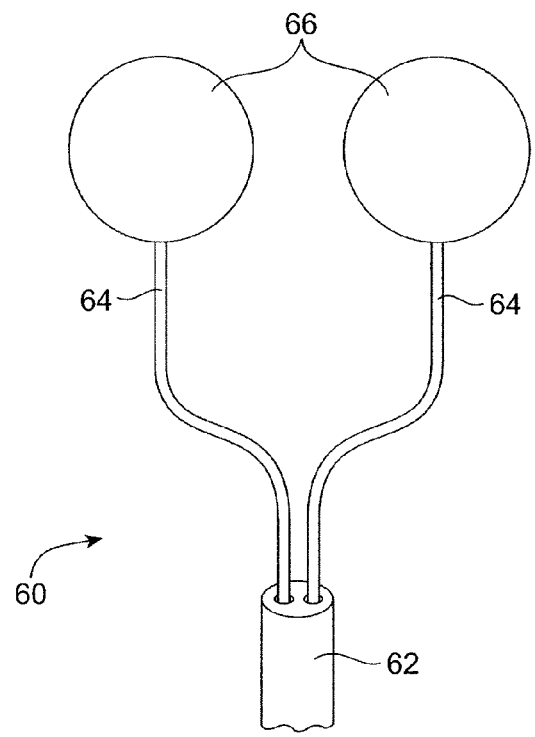
FIG. 7 is a perspective view of a distal portion of a catheter apparatus having two expandable members coupled with two prongs according to another embodiment of the present invention.

FIG. 7 shows another embodiment of a catheter device 60, which includes a catheter body 62, a two-pronged tissue apposition member 64, and two expandable members 66 coupled to the two prongs 64 for providing further tissue apposition. Tissue apposition member 64, the prongs of which may comprise nitinol, some other shape memory material, or the like, is typically released from catheter body 62 within a PFO to allow the prongs 64 to expand apart. The tissue between the prongs is thus brought together, in essence flattening or "fish-mouthing." For further tissue apposition expandable members 66 may be expanded, and optionally, proximal force may be applied, such as by pulling back on catheter body 62, to urge the tissues together with expandable members 66. Prongs 64 then act as energy transmission members for applying energy to the tissues. Typically, prongs 64 are bipolar RF energy transmission members, but alternative embodiments are also contemplated.

Figure 8:
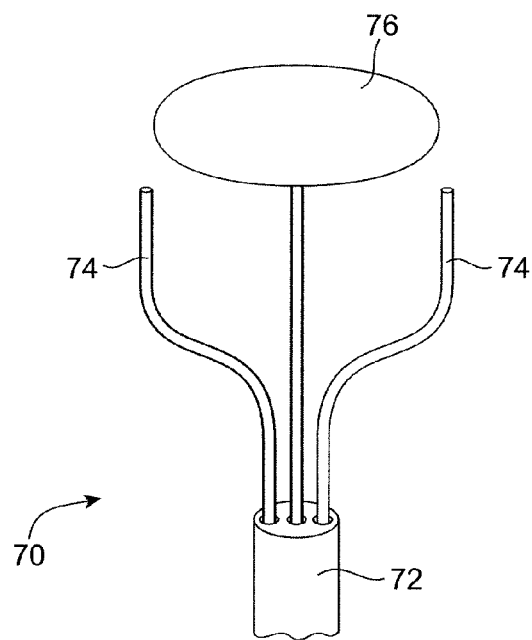
FIG. 8 is a perspective view of a distal portion of a catheter apparatus having one expandable member and two prongs according to another embodiment of the present invention.

In an alternative embodiment, and referring now to FIG. 8, a catheter device 70 may include a catheter body 72, a two-pronged tissue apposition member 74, and a separate expandable member 76 for enhancing tissue apposition. Again, tissue apposition members 74 may also act as energy transmission members. Additionally or alternatively, apertures may be provided in expandable member 76 for introducing conductive fluid as a portion of the energy delivery system.

Figure 9:
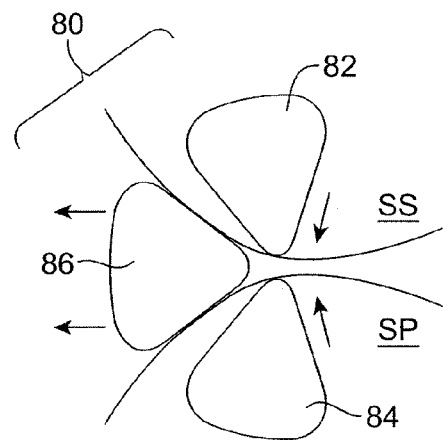
FIG. 9 is a cross-sectional view of a distal portion of a catheter apparatus having two tissue apposition members and a shaped catheter body according to another embodiment of the present invention.

With reference now to FIG. 9, in another embodiment a catheter device 80 suitable includes a catheter body 86, a first tissue apposition member 82 and a second tissue apposition member 84. As mentioned previously, one or both of tissue apposition members 82, 84 may be coupled with or may act as energy transmission members. In this embodiment, first tissue apposition member 82 is configured to contact tissue from the right atrium, such as septum secundum tissue SS, while second apposition member 84 is configured to contact tissue from the left atrium, such as septum primum tissue SP. In contacting and bringing these tissues together (hollow-tipped arrows), tissue apposition members 82, 84 also bring the tissues together (or squeeze the tissues) against catheter body 86. When force is applied against catheter body 86, it is urged to one side (solid-tipped arrows), due to its cross-sectional shape. In the embodiment shown, catheter body 86 has a triangular cross-section, though in alternative embodiments it may have other shapes, such as oval, ellipsoid, diamond-shaped, or the like. When catheter body 86 is urged aside, tissue apposition/energy transmission members 82, 84 are used to apply energy to tissue in a first location. Apposition members 82, 84 may then be moved to the side, toward catheter body 86, to bring adjacent tissues together, thus urging catheter body 86 further along the PFO. Energy may then be applied again to the tissue in the second location. Using such a technique, it may be possible to move catheter device 80 across a PFO from one side to another, applying energy and closing the PFO as device 80 is moved. In other words, catheter devices "walks" along the PFO, spot tissue welding as it goes.

Figure 10:
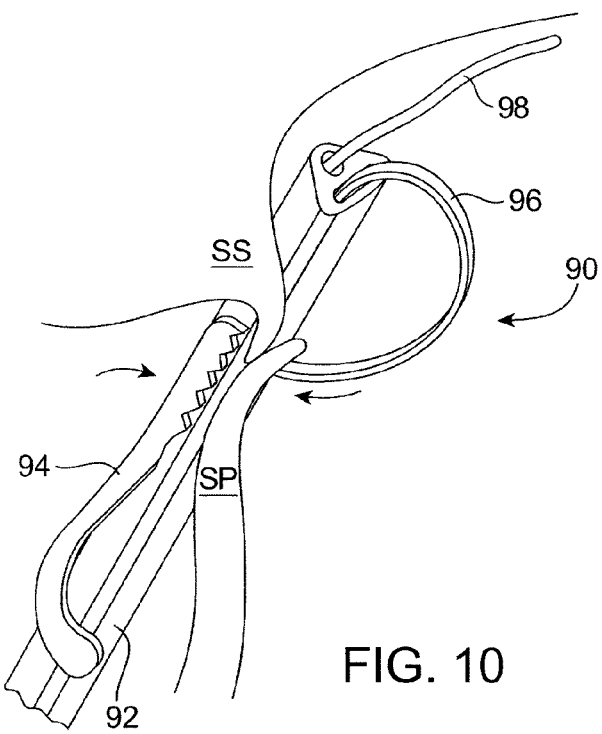
FIG. 10 is a perspective view of a distal portion of a catheter apparatus having two tissue apposition members and a shaped catheter body according to another embodiment of the present invention.

FIG. 10 shows one embodiment of a catheter device 90 which may be used in a method similar to the one just described. Device 90 includes a catheter body 92, a first tissue apposition member 94, and a second tissue apposition member 96, and is shown disposed over a guidewire 98. In this embodiment, tissue apposition members 94, 96 also act as energy transmission members. First tissue apposition member 94 is a spring-loaded jaw, and second tissue apposition member 96 is a shape-memory energy transmission member, such as an electrode. As described above, when tissue apposition members 94, 96 bring tissue adjacent the PFO together, they bring the tissue together against catheter body 92, thus squeezing catheter body 92 aside. After applying energy to the tissues, tissue apposition members 94, 96 may then be moved toward catheter body 92 again and used to bring tissue together again, thus squeezing catheter body 92 aside again. To enhance such a technique, catheter body 92 may include one or more slick or slippery surfaces, to allow it to more easily slide to the side. Catheter body 92 may also include a coating of a tissue welding substance, solder or the like, such as albumin, which partially rubs off each time catheter body is squeezed aside, thus enhancing application of energy to the tissues to close the PFO. Catheter body 92 may further include one or more apertures for introducing a fluid at the location of energy application, to act as a welding fluid or to otherwise enhance tissue welding.

In the embodiments described in FIGS. 9 and 10, as well as in other embodiments, a catheter device may also include a biasing member for biasing the catheter device toward one side of a PFO to start a PFO closure procedure. For example, an expandable member may be coupled with a catheter body, typically on one side of the body, such that when the catheter device is positioned in the PFO and the expandable member is expanded, the catheter device is urged to one side of the PFO. Tissue may then be brought together and welded at that side and the expandable member may be gradually deflated to allow the catheter device to move toward the other side of the PFO, bringing tissue together and applying energy as it goes. A similar result may be achieved with a biasing wire, a catheter body having a biasing shape, or the like.

Figures 11A, 11B:
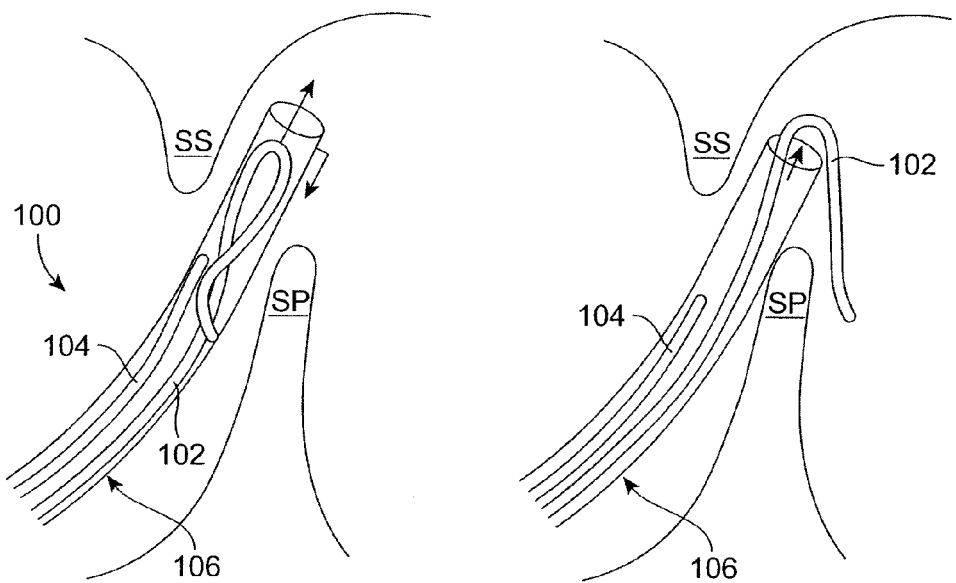
FIGS. 11A-11C are perspective views of a distal portion of a catheter apparatus, demonstrating a method for bringing tissues together according to another embodiment of the present invention.
Figure 11C:
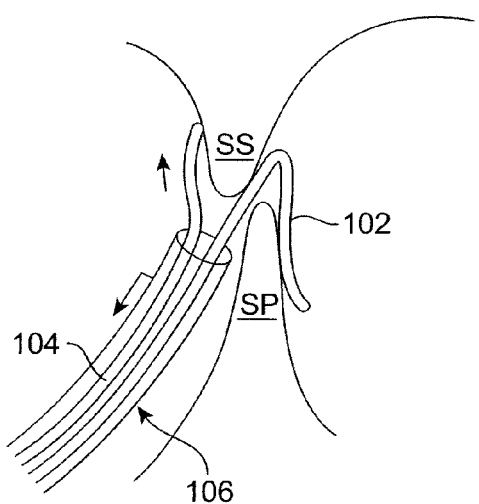

Referring now to FIGS. 11-11C, in another embodiment a catheter device 100 for treating a PFO includes a catheter body 106, a first tissue apposition member 104 and a second tissue apposition member 102. Tissue apposition members 102, 104 comprise shape memory material energy transmission members made of nitinol or any other suitable shape memory material(s). To deploy tissue apposition members 102, 104, catheter body 106 is first advanced through the PFO, as shown in FIG. 11A. Catheter body 106 is then withdraw/retracted and second tissue apposition member 102 is advanced (solid-tipped arrows), so that second tissue apposition member 102 is released from the distal end of catheter body 106. As shown in FIG. 11B, catheter body 106 may then be advanced again to push against a surface of second tissue apposition member 102, thus opening apposition member 102 (solid-tipped arrows) to fit over PFO-adjacent tissue such as the septum primum. This technique is analogous to expanding the tines of a bobby pin. As shown in FIG. 11C, after second tissue apposition member 102 is placed in contact with the septum primum, catheter body 106 may be retracted again and first tissue apposition member 104 may be advanced to expose first member 104. Tissues are them brought together between the two apposition members 102, 104 and the members 102, 104 are used to apply energy to the tissues to close the PFO.

Figure 12A:
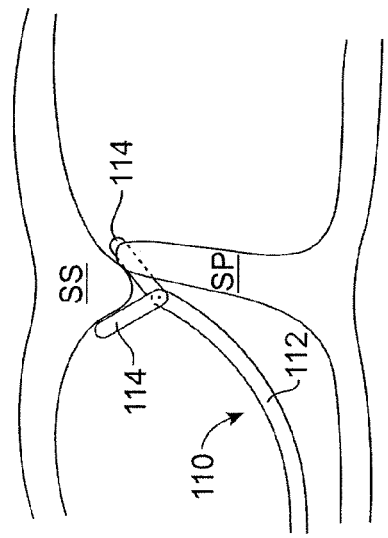
FIGS. 12A and 12B are perspective views of a distal portion of a catheter apparatus having opposable jaws according to another embodiment of the present invention.
Figure 12B:
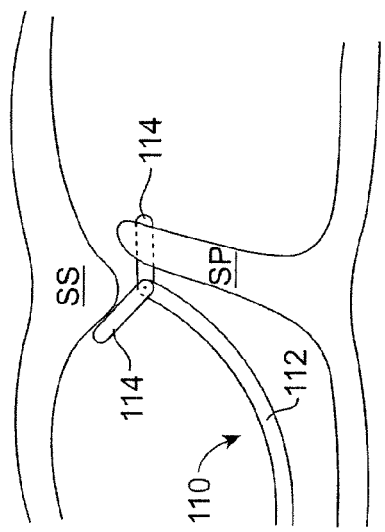

FIGS. 12A and 12B show another embodiment of a catheter device 110 for treating PFO, including a catheter body and a pair of opposable jaws 114. Jaws 114 may be used to grasp tissue adjacent the PFO, such as septum secundum SS and septum primum SP tissues, to bring them together for energy application and tissue welding. Jaws 114 may also comprises energy transmission members, such as two electrodes of a bipolar RF device, one electrode and one energy return member of a monopolar RF device, or the like. In some embodiments, one or both jaws 114 may be advanced through (or in other words pierce into) PFO tissues. Here, as designated by the dotted lines, one jaw is advanced into septum primum SP tissue. FIG. 12A shows jaws 114 expanded, and FIG. 12B shows jaws 114 drawn together to draw the tissues together.

Figure 13A:
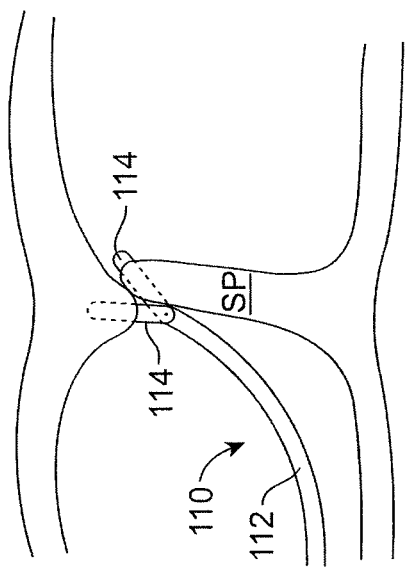
FIGS. 13A and 13B are perspective views of a distal portion of a catheter apparatus having opposable jaws according to another embodiment of the present invention.
Figure 13B:
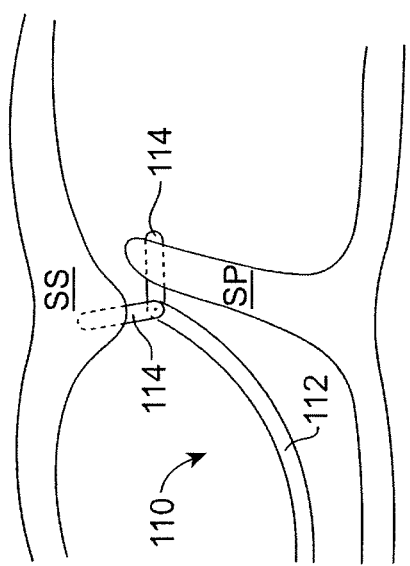

Referring to FIGS. 13A and 13B, catheter device 110 is shown with both jaws 114 piercing tissue adjacent the PFO. Again, jaws 114 are expanded in FIG. 13A and drawn together in 13B to bring the tissues into apposition.

Figure 14:
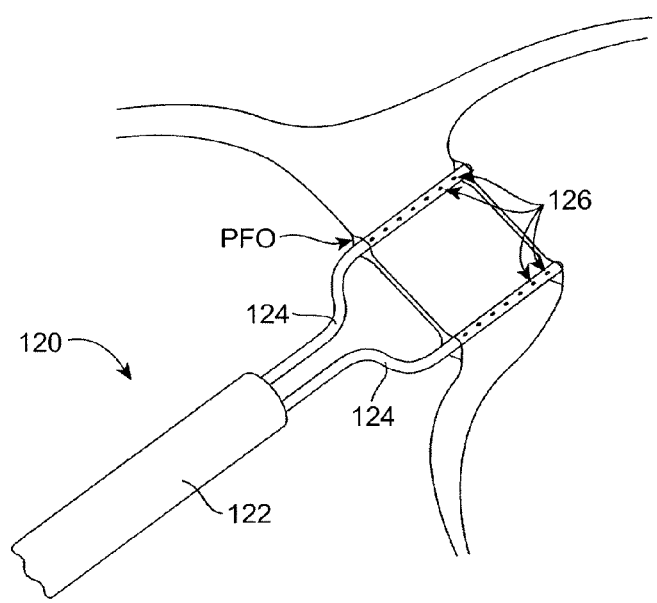
FIG. 14 is a perspective view of a distal portion of a catheter apparatus having a two-prong tissue apposition member with vacuum according to another embodiment of the present invention.

Referring now to FIG. 14, in one embodiment a catheter device 120 for treating PFO suitably include a catheter body 122 and a two-pronged, "fish mouth" tissue apposition member 124 having multiple vacuum apertures 126 for applying a vacuum force to enhance tissue apposition. As already described, tissue apposition prongs 124 may be deployed inside the PFO to bring tissues together, and vacuum apertures 126 may then be used to further appose the tissues. Energy may then be applied via tissue apposition prongs 124, which may comprise bipolar RF energy transmission members in one embodiment.

Figure 15A:
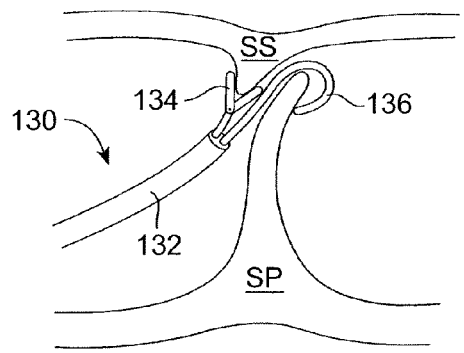
FIGS. 15A and 15B are perspective views of a distal portion of a catheter apparatus having opposable jaws and a curved member according to another embodiment of the present invention.
Figure 15B:
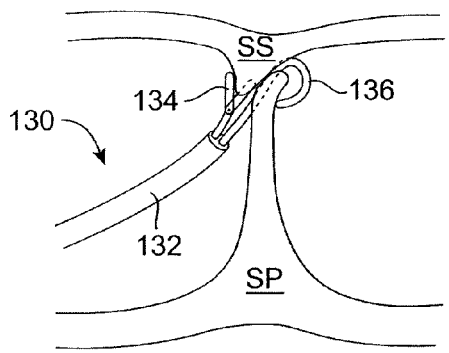

With reference to FIGS. 15A and 15B, another embodiment of a catheter device 130 suitably includes a catheter body 132, a grasping tissue apposition member 134, and a shape memory tissue apposition member 136. These tissue apposition members 134, 136 may be used to contact tissue from right and left atrial sides of the PFO, as in FIG. 15A, and then used to bring the tissues together, as in FIG. 15B. Either or both tissue apposition members 134, 136 may also act as energy transmission members.

Figure 16A:
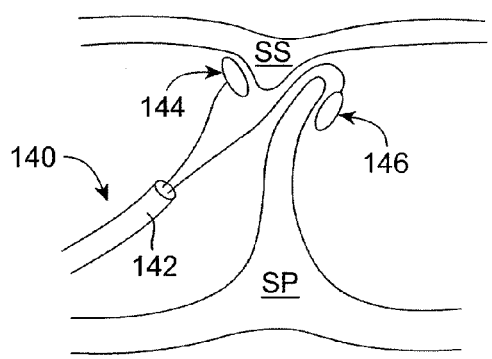
FIGS. 16A and 16B are perspective views of a distal portion of a catheter apparatus having magnetic tissue apposition members according to another embodiment of the present invention.
Figure 16B:
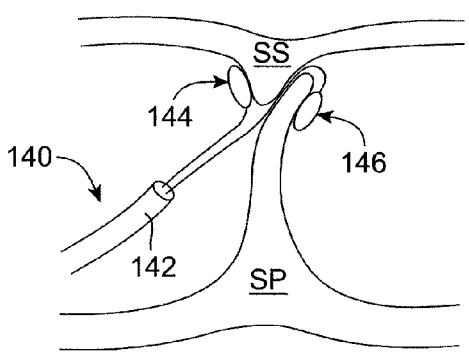

In FIGS. 16A and 16B, a catheter device 140 includes a catheter body 142, a positively charged magnet 144 and a negatively charged magnet 146. The magnets 144, 146 act as both tissue apposition members and energy transmission member and bring tissue together between them due to their opposite polarities, as shown in FIG. 16B.

Figure 17:
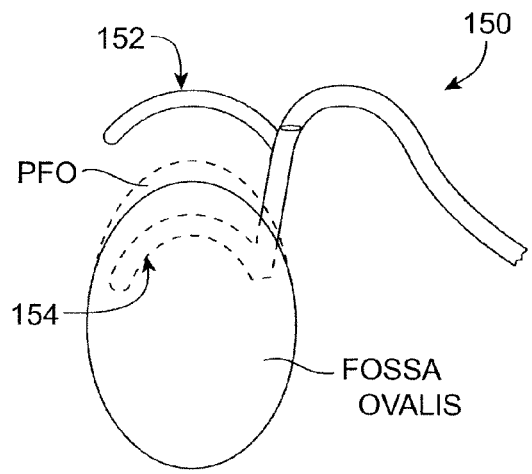
FIG. 17 is a perspective view of a distal portion of a catheter apparatus having clamping tissue apposition members according to another embodiment of the present invention.

In another embodiment, as shown in FIG. 17 in a perspective from inside the right atrium, a tissue apposition member 150 of a catheter device for treating PFO may comprise a clamp, including a first clamp arm 152 for positioning in the right atrium and a second clamp arm 154 for positioning in the left atrium. The arms 152, 154 are then brought together to bring the tissues together.

Figure 18:
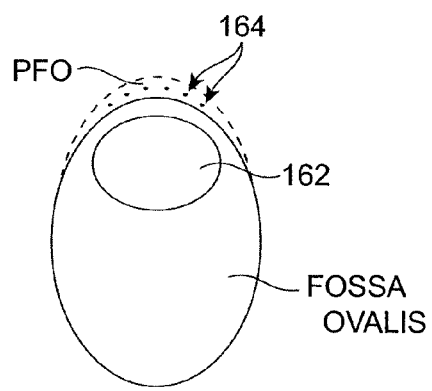
FIG. 18 is a right atrial view of a PFO with a stationary energy transmission member in the right atrium and multiple tissue welds according to another embodiment of the present invention.

In FIG. 18, again from a perspective from inside the right atrium, only an electrode 162 is shown. In one embodiment of the device, a relatively large electrode 162 may be positioned in the right atrium and maintained in approximately the same position throughout a procedure. A smaller electrode may then be disposed in the left atrium and moved along the tissues of the PFO to create spot tissue welds 164 to close the PFO. Pressure and bipolar RF energy is directed between the smaller electrode and the larger electrode 162, to bring the tissue together and apply energy to close the PFO.

Figure 19:
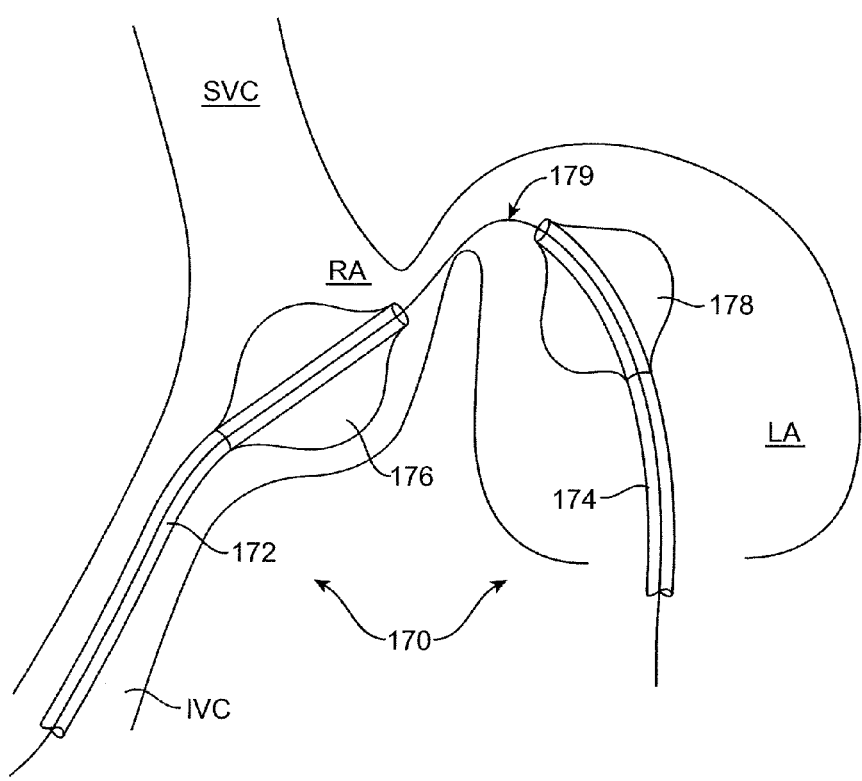
FIG. 19 is a perspective view of a distal portion of a catheter apparatus having two expandable members and a guidewire extending through the right and left atria of the heart according to another embodiment of the present invention.

Referring now to FIG. 19, in yet another embodiment, a catheter system 170 for treating PFO may include a first catheter body 172 having a first expandable member 176, a second catheter body 174 having a second expandable member 178 and a guidewire 179. In one embodiment, guidewire extends from an entry point on the patient, such as a femoral vein, through the inferior vena cava IVC, right atrium RA, PFO and left atrium LA, and then through the left ventricle, aorta, and eventually out a femoral artery. Catheter bodies 172, 174 may be advanced to locations in the right and left atria respectively along this guidewire. In an alternative embodiment, two guidewires may be used, and they may be coupled within the PFO or elsewhere within the heart.

In another embodiment, as shown in FIGS. 20A-20C, a catheter device 180 includes a catheter body 182, a left atrial tissue apposition member 184 and a separate right atrial tissue apposition member 186. FIG. 20A shows just catheter body 182 and left atrial member 184 from a right atrial view, with left atrial member 184 hooking over the PFO into the left atrium. FIG. 20B is a close-up view from the perspective of the distal end of left atrial member 184 hooking into the left atrium. FIG. 20C shows both left atrial member 184 and right atrial member 186 in place for apposing PFO tissues. In one embodiment, left atrial member 184 may be rotated (curved arrow) to move the hooked portion along the left atrial surface of the PFO to apply energy at multiple locations.

Referring to FIG. 21A, one embodiment of a backstop catheter device 800 for treating a PFO may include an outer catheter element 802, an inner catheter element 804, a backstop 806 coupled with a portion 808 extending through the inner shaft 804, and energy delivery arms 810. Energy delivery arms 810 can include ultrasound transducers, microwave antennae, or RF electrodes. The backstop catheter device 800 is advanced through the PFO and used to help advance an energy delivery catheter to the right atrial side of the PFO. Relative translation of an inner 804 and outer catheter element 802 deploy a set of arms 810 which carry the energy delivery elements. The energy delivered breaks down the collagen in each part of the PFO, and allows the tissues to be welded together. The energy delivered could take the form of RF, microwave, or ultrasound. RF energy can either be monopolar, in which the backstop 806 is electrically insulated such that it is not part of the energy delivery path, or bipolar, in which case the backstop 806 acts as the energy return electrode. If desired, the inner catheter 804 of the energy delivery catheter 800 can be used to infuse liquid albumin to act as a protein solder for the system. Alternatively, the shaft of the backstop 806 could be covered with a tube of solid or braided material made of, or soaked in, a tissue solder. After delivery of the energy and activation and bonding of the tissue solder to the PFO walls, the backstop 806 is withdrawn through the PFO and the entire system is withdrawn.

As illustrated in FIG. 21B, in another embodiment, a catheter device 820 can include an expandable balloon member 822 and an expandable backstop 824. The balloon catheter 820 can be outfitted with sections 826 of piezo film/foil which can be driven electrically to produce an ultrasound signal to heat and seal a PFO. The balloon member 822 and expandable backstop 824 are used to position the catheter device 820 in the desired location and energy is then applied via the piezo film/foil 826 for treating the PFO.

In other embodiments, PFO closure systems according to the present invention may utilize one or more clips to close the PFO. Such systems can be divided into designs that involve both a right and left atrial component, and those that are right-sided only. While they are generally not energized, it may be desirable to add energy to any of these designs to facilitate adhesion and sealing.

Referring now to FIG. 22A through FIG. 22D, another embodiment of the present invention is described which includes a catheter device 832 comprising a coil closure device 830. According to this embodiment, a catheter 832 is used to insert a closure device 830 comprising a pair of flexible, pre-formed coils 834, 836 into both the left and right atriums. The spring tension in the pair of coils 834, 836 pulls the primum into the secundum to close the PFO.

Referring now to FIG. 23, another embodiment of the present invention includes a deployable spring coil closure device 840 which may inserted through a small pierced hole in the septum. For example, a needle tipped catheter (not shown) can be used to pierce the primum and install the spiral spring coil 840 (e.g., similar to that described above) through a small hole made in the septum rather than through the PFO tunnel itself.

Referring now to FIG. 24, in another embodiment, a spiral spring coil 850 is inserted through the PFO. The portion 852 of the wire form that goes through the actual PFO tunnel is shaped to maximize contact area and flatten the PFO by stretching it closed. RF energy is then applied to the wire 850 to burn it into the tissue and promote tissue growth, especially in the area between the primum and secundum where there is a high contact area. The flattened PFO combined with tissue healing on adjacent primum and secundum sides might cause the PFO to heal closed. The spring tension provided by the spiral spring coil 850 will keep the PFO closed as the tissue heals. The tissue healing around the wire 850 will help secure it to the tissue and prevent embolization.

In another embodiment, a patch might also be used on the right atrial side to provide an additional means to seal the PFO. If it is desirable to prevent the wire around the patch area from receiving RF energy, it is possible to electrically insulate the portion of the wire that is not desired to burn into the tissue (not shown). In another embodiment, the "zig zag" portion 852 of the coil 850 located in the flattened passageway between the primum and secundum might have sharp features (such as needles or barbs) which cause the adjacent surfaces of the primum and secundum to bleed and heal together. RF energy might be used in any of the embodiments of the spiral spring coil described above to burn some or all of the device into the tissue and promote rapid healing and prevent embolization.

Although the foregoing description is complete and accurate, it describes only exemplary embodiments of the invention. Various changes, additions, deletions and the like may be made to one or more embodiments of the invention without departing from the scope of the invention. Additionally, different elements of the invention could be combined to achieve any of the effects described above. Thus, the description above is provided for exemplary purposes only and should not be interpreted to limit the scope of the invention as set forth in the following claims.

The invention claimed is:

1. A catheter device for treating a patent foramen ovale in a heart, the heart including a septum secundum tissue and a septum primum tissue adjacent the patent foramen ovale, the catheter device comprising:
   an elongate catheter body having a proximal end and a distal end;
   a first tissue apposition member and a second tissue apposition member located at or near the catheter body distal end and configured to move so as to bring the septum primum and septum secundum tissues adjacent the patent foramen ovale at least partially together, the first tissue apposition member being configured contact the septum secundum tissue adjacent the patent foramen ovale from a right atrium of the heart without penetrating the septum secundum tissue, the second tissue apposition member being configured to pierce into the septum primum tissue of the heart; and at least one energy transmission member at or near the distal end for applying energy to the tissues to substantially close the patent foramen ovale acutely, wherein the first and second tissue apposition members comprise a clamp for clamping the tissues together.

2. A method for treating a patent foramen ovale in a heart with a catheter device, the heart including a septum secundum tissue and a septum primum tissue adjacent the patent foramen ovale, the method comprising:

positioning an elongate catheter body having a proximal end and a distal end, such that the distal end is adjacent the patent foramen ovale;

moving a first tissue apposition member and a second tissue apposition member, which are disposed at or near the distal end of the catheter body, so as to bring the septum primum and septum secundum tissues adjacent the patent foramen ovale at least partially together, the first tissue apposition member being moved to contact the septum secundum tissue adjacent the patent foramen ovale from a right atrium of the heart without penetrating the septum secundum tissue, and the second tissue apposition member being moved to pierce into the septum primum tissue of the heart; and applying energy to the primum and septum secundum tissues, via at least one energy transmission member disposed at or near the distal end of the catheter body, to substantially close the patent foramen ovale acutely.

* * * * *